US010610229B2

(12) United States Patent
Jönsson

(10) Patent No.: US 10,610,229 B2
(45) Date of Patent: Apr. 7, 2020

(54) TEMPORARY EMBOLIC PROTECTION DEVICE AND MEDICAL PROCEDURE FOR DELIVERY THEREOF

(75) Inventor: Anders Jönsson, Bromma (SE)

(73) Assignee: SWAT Medical AB, Helsingborg (SE)

(*) Notice: Subject to any disclaimer, the term of this patent is extended or adjusted under 35 U.S.C. 154(b) by 0 days.

(21) Appl. No.: 13/062,499

(22) PCT Filed: Sep. 4, 2009

(86) PCT No.: PCT/EP2009/061509
§ 371 (c)(1),
(2), (4) Date: Aug. 16, 2011

(87) PCT Pub. No.: WO2010/026240
PCT Pub. Date: Mar. 11, 2010

(65) Prior Publication Data
US 2011/0295304 A1    Dec. 1, 2011

Related U.S. Application Data

(60) Provisional application No. 61/094,283, filed on Sep. 4, 2008.

(30) Foreign Application Priority Data

Sep. 4, 2008  (SE) ...................... 0801901

(51) Int. Cl.
*A61F 2/01*   (2006.01)
*A61B 17/12*  (2006.01)

(52) U.S. Cl.
CPC .... *A61B 17/12109* (2013.01); *A61B 17/1204* (2013.01); *A61B 17/12036* (2013.01);
(Continued)

(58) Field of Classification Search
CPC ............. A61F 2/01–013; A61F 2002/011–018
(Continued)

(56) References Cited

U.S. PATENT DOCUMENTS 6,235,044 B1    5/2001  Root et al.
6,245,088 B1 *  6/2001  Lowery ........................ 606/200
(Continued)

FOREIGN PATENT DOCUMENTS

WO    WO 97/42878 A1   11/1997
WO    WO 99/12478 A1    3/1999
(Continued)

OTHER PUBLICATIONS

European International Searching Authority, International Preliminary Report on Patentability in PCT/EP2009/061509 dated Oct. 28, 2010, 12 pages.
(Continued)

*Primary Examiner* — Jonathan A Hollm
(74) *Attorney, Agent, or Firm* — Inskeep IP Group, Inc.

(57) ABSTRACT

An embolic protection device, kit, and medical procedure prevent embolic material from entering into side branch vessels of the aortic arch. The device is a collapsible embolic protection device devised for temporary transvascular delivery to an aortic arch of a patient and has a protection unit that comprises a selectively permeable unit adapted to prevent embolic material from passage with a blood flow into a plurality of aortic side branch vessels at the aortic arch. The protection unit is permanently attached to a transvascular delivery unit and a first support member that is at least partly arranged at a periphery of the selectively permeable unit. In an expanded state of the device, the connection point is enclosed by the first support member or arranged at said support member.

23 Claims, 10 Drawing Sheets

(52) U.S. Cl.
CPC .. *A61B 17/12159* (2013.01); *A61B 17/12172* (2013.01); *A61F 2/01* (2013.01); *A61F 2/013* (2013.01); *A61B 2017/1205* (2013.01); *A61F 2002/018* (2013.01); *A61F 2230/0008* (2013.01); *A61F 2230/0069* (2013.01); *A61F 2230/0076* (2013.01); *A61F 2230/0093* (2013.01)

(58) Field of Classification Search
USPC .................................................. 606/108, 200
See application file for complete search history.

(56) References Cited

U.S. PATENT DOCUMENTS

| | | | |
|---|---|---|---|
| 6,258,120 | B1 | 7/2001 | McKenzie et al. |
| 6,348,063 | B1* | 2/2002 | Yassour et al. ............... 606/200 |
| 6,361,545 | B1 | 3/2002 | Macoviak et al. |
| 6,689,150 | B1 | 2/2004 | Van Tassel et al. |
| 8,062,324 | B2 | 11/2011 | Shimon et al. |
| 2002/0002383 | A1* | 1/2002 | Sepetka et al. ............... 606/200 |
| 2002/0143362 | A1* | 10/2002 | Macoviak et al. ............ 606/200 |
| 2002/0169437 | A1* | 11/2002 | Macoviak et al. ............ 604/509 |
| 2003/0004539 | A1* | 1/2003 | Linder .................... A61F 2/013 606/200 |
| 2003/0153943 | A1* | 8/2003 | Michael ................. A61F 2/013 606/200 |
| 2003/0171803 | A1 | 9/2003 | Shimon |
| 2004/0215167 | A1* | 10/2004 | Belson ...................... A61F 2/01 604/526 |
| 2005/0216031 | A1* | 9/2005 | White .............. A61B 17/22031 606/114 |
| 2006/0015138 | A1* | 1/2006 | Gertner ..................... A61F 2/01 606/200 |
| 2006/0020285 | A1* | 1/2006 | Niermann ................. A61F 2/01 606/200 |
| 2006/0025806 | A1 | 2/2006 | Krolik et al. |
| 2006/0161241 | A1* | 7/2006 | Barbut et al. ................ 623/1.15 |
| 2006/0253148 | A1* | 11/2006 | Leone ............. A61B 17/12022 606/200 |
| 2007/0088383 | A1* | 4/2007 | Pal et al. ..................... 606/200 |
| 2007/0270901 | A1* | 11/2007 | Shimon ..................... A61F 2/01 606/200 |
| 2008/0065145 | A1* | 3/2008 | Carpenter .................... 606/200 |
| 2008/0147111 | A1 | 6/2008 | Johnson et al. |
| 2009/0254172 | A1* | 10/2009 | Grewe ......................... 623/1.15 |
| 2014/0257366 | A1 | 9/2014 | Jönsson |

FOREIGN PATENT DOCUMENTS

| | | |
|---|---|---|
| WO | WO99/32050 A1 | 7/1999 |
| WO | WO1999032050 A1 | 7/1999 |
| WO | WO 2007/035885 A2 | 3/2007 |
| WO | WO 2007/149107 A1 | 12/2007 |
| WO | WO 2008033845 A2 * | 3/2008 |
| WO | WO 2009/049677 A1 | 4/2009 |

OTHER PUBLICATIONS

European International Searching Authority, International Search Report in PCT/EP2009/061509 dated Nov. 23, 2009, 4 pages.

* cited by examiner

TEMPORARY EMBOLIC PROTECTION DEVICE AND MEDICAL PROCEDURE FOR DELIVERY THEREOF

RELATED APPLICATIONS

This application claims priority to International Patent Application No. PCT/EP2009/061509, International Filing Date 4 Sep. 2009, entitled Temporary Embolic Protection Device And Medical Procedure For Delivery Thereof; to Swedish Patent Application 0801901-0 filed 4 Sep. 2008 entitled Embolic Protection Device And Medical Procedure For Delivery Thereof; and to U.S. Provisional Application Ser. No. 61/094,283 filed 4 Sep. 2008 entitled Embolic Protection Device And Medical Procedure For Delivery Thereof, all of which are hereby incorporated herein by reference in their entireties.

FIELD OF THE INVENTION

This invention pertains in general to the field of medical devices and medical procedures applying such medical devices. More particularly, the invention relates to an embolic protection device preventing undesired embolic material from entering one or more branch vessels of a main vessel, such as the aortic arch, as well as a method of deploying such a device in the aortic arch for cerebral protection.

BACKGROUND OF THE INVENTION

Cerebral embolism is a known complication of cardiac surgery, cardiopulmonary bypass and catheter-based interventional cardiology and electrophysiology procedures. Embolic particles, which may include thrombus, atheroma and lipids, may become dislodged by surgical or catheter manipulations and enter the bloodstream, embolizing in the brain or other vital organs downstream. Cerebral embolism can lead to neuropsychological deficits, stroke and even death. Prevention of cerebral embolism benefits patients and improves the outcome of these procedures.

Various embolic protection devices are known in the art. An embolic protection device for side branch vessels of the aortic arch has for instance been disclosed in US 2004/0215167. This embolic protection device has an expandable tubular structure supporting a filter mesh material. The embolic protection device is compressed to a small diameter for insertion into a patient's aorta, and then expanded within the aorta with the filter mesh material positioned to allow blood to enter side branch vessels connected to the aorta and to prevent embolic material from entering the side branch vessels. The device is deployed and left in place for long-term protection. Alternatively, the device may be compressed and withdrawn from the aorta.

However, the embolic protection devices disclosed in 2004/0215167 have a number of drawbacks. The device may be difficult to extract from the aortic arch as a stent like design is devised for permanent implantation and removing a stent may harm the implantation site. The device also forms along the aorta and may at least partly be pressed against or into the ostia regions of the side vessels. Most often these ostia regions are subject to sedimented plaque on the outside of the tissue in these ostia regions. When a stent like device is pressed against the plaque, the latter loosens from the tissue on which it is situated and is washed along the side branch vessels as debris. However, this debris is an undesired embolic material, which the device should avoid to enter the branch vessels.

In U.S. Pat. No. 6,258,120 implantable cerebral protection device is disclosed for diverting emboli away from the carotid arteries in the aorta. The disclosed devices are aortic diverters that generally comprise a hollow tube with a substantially cylindrical or conical wall, which is impermeable to emboli and which has open ends that allow blood to enter one end, flow through the tube and exit the other end. The proximal end of the hollow tube is circumferentially sized to completely fill the lumen of the aorta. Additionally, snowshoe aortic diverters, which are planar rather than cylindrical, are also disclosed. The methods disclosed in U.S. Pat. No. 6,258,120 include the steps of providing an aortic diverter carried by an intravascular catheter, introducing the intravascular catheter into the vascular system, advancing the intravascular catheter into the aortic arch to the region of the carotid arteries, and deploying the aortic diverter.

However, like the devices disclosed in US 2004/0215167, the devices and methods of U.S. Pat. No. 6,258,120 may damage the aortic vessel wall. Furthermore, a leakage of embolic material into the side branch vessels of the aortic arch may be present, e.g. past the periphery of the tubular structure, or of the snowshoe like embodiments disclosed. Moreover, the devices disclosed may, at least partly, contact the ostia of the side branch vessels, and thus set free embolic debris from the ostia which is carried to the carotid arteries and may lead to cerebral damage. Further, a backflow carrying embolic material may occur from the distal end of the devices of U.S. Pat. No. 6,258,120 into the side branch vessels. The snowshoe like devices have and attached handle or cannula and need to be installed by means of open chest surgery comprising incising the aorta, which has numerous drawbacks compared to intravascular delivery, including aortic trauma. The devices need to be secured to the lumen of the aorta through various mechanisms including sutures, surgical clips, hooks, adhesive material, substantially rigid sleeves, or frictional engagement. Such securing is difficult to accomplish in a reliable manner via transvascular access.

In US 2008/0065145 an embolic protection device and method of use are disclosed. A blood debris deflector umbrella is disclosed, which has a blood flow permeable covering. The umbrella is extending over the ostia of the brachiocephalic artery and the left carotid artery. The deflector is inserted percutaneously and placed by means of a catheter, either via the right arteria subclavia ending in the aortic arch via the brachiocephalic artery, or the femoral artery and into the brachiocephalic artery and the right arteria subclavia. However, the device has in any case a guide wire arranged extending between the aortic arch and the brachiocephalic artery, which is to be protected by the device. This means that, like in the aforementioned disclosures, the device will inevitably be intravascularly manipulated and thus it will likely contact the ostia of the brachiocephalic artery, i.e. the side branch vessel of the aorta leading to the right carotid artery. Thus a risk for iatrogenic caused embolization is present, i.e. the physician likely will set free embolic debris from the ostia of the brachiocephalic artery when using the device. The embolic debris is carried to the right carotid artery and may lead to cerebral damage.

Moreover, the dome shaped device of US 2008/0065145 appears to be difficult, to work in practice due to the anatomical structure and position of the afore described access way via the brachiocephalic artery. The device will have to be very large in order to cover the ostia of the brachiocephalic artery and the left carotid artery. Thus the device will be very voluminous in the aortic arch.

Hence, known cerebral embolic protection devices have shortcomings, including: difficult to position in a vessel, and even more difficult to position in two vessels; they may cause damage to the vessel wall and potentially cause an emboli themselves; they are hindering surgeons when trying to achieve a good result with some intended intervention/operation; visualization of the protective device may impair visualization of other components used during concurrent medical procedures; they may cause impaired flow if they are designed to collect the embolic material.

Thus, there is a need for a new, or improved, or alternative device, or method for preventing embolic material from entering branch vessels, such as the aortic arch side branch vessels, and/or from creating debris from the ostia of the aortic arch side branch vessels that may be carried towards the brain of a patient during a medical procedure.

Hence, an improved embolic protection device or method would be advantageous.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a device or method according to the appended patent claims for providing temporary embolic protection to a patient's aortic arch vessels during medical procedures, such as cardiac surgery and interventional cardiology and electrophysiology procedures. Embolic particles in the aortic blood flow are prevented from entering the aortic arch side branch vessels, including the carotid arteries that lead to the brain.

According to one aspect of the invention, a device is provided. The device is a collapsible embolic protection device devised for temporary transvascular delivery to an aortic arch of a patient, the device having a protection unit comprising a selectively permeable material or unit adapted to prevent embolic material from passage with a blood flow into a plurality of aortic side branch vessels at the aortic arch, wherein the protection unit is permanently or releasably (for assembly prior to introduction into the body) attached to a transvascular delivery unit at a connection point or region, or an attachment point, provided at the selectively permeable unit, and a first support member for the protection unit that is at least partly arranged at a periphery of the selectively permeable unit. In an expanded state of the device, the connection point is enclosed by the first support member or integral therewith, wherein the transvascular delivery unit is connected off-center to the protection unit at the connection point. In some embodiments, the connection point or region, or attachment point, is enclosed by the first support member.

In embodiments the device is devised for percutaneous transvascular delivery to the aortic arch through one of the aortic side branch vessels that is different from aortic side branch vessels leading to the head or neck of the patient such as the brachiocephalic artery and the left carotid artery, in a collapsed state.

In embodiments the device is devised for percutaneous transvascular delivery through one of the aortic side branch vessels different than the aortic side branch vessels temporary protected by the device when delivered to the aortic arch.

In embodiments the aortic side branch vessel for the delivery is the left subclavian artery of the patient, for instance directly accessed via a puncture in a vessel of the left arm of the patient.

In embodiments the device is devised to extend over the ostia of a first, second and third of the side branch vessels, wherein the first side branch vessel is the left subclavian artery, the second side branch vessel is the left common carotid artery, and the third side branch vessel is the brachiocephalic artery.

The connection point may be provided at the selectively permeable unit or at the first support member.

The first support member may be shaped to apposition to tissue of a vessel wall portion of the aortic arch or releasably engage with the tissue of the vessel wall portion, and wherein the first support member is formed to encircle a plurality of ostia regions of the aortic side branch vessels into the aortic arch, and at a distance to the ostia regions, such that the selectively permeable unit is arranged to separate a first fluid volume of the aortic side branch vessels from a second fluid volume in the aortic arch when the protection unit is positioned in the aortic arch.

The connection point may be provided on a surface of the selectively permeable unit devised to be oriented towards the aortic side branch vessels from inside the aortic arch and at a distance from the ostia regions when the protection unit is positioned in the aortic arch.

The selectively permeable unit is in embodiment non-tubular, extending substantially planar in the expanded state.

The selectively permeable unit may be non-tubular, extending substantially in form of a flat umbrella, parachute, or mushroom which opening edge is formed by the first support member and which opening is devised to be oriented towards the aortic side branch vessels from inside the aortic arch when the protection unit is positioned in the aortic arch, in the expanded state, and wherein the delivery unit is at least partly arranged in the left subclavian artery.

The selectively permeable unit may be devised to be arranged at a distance from ostia regions of the aortic side branch vessels of the aortic arch, when the protection unit is positioned in the aortic arch, in the expanded state.

The first support member may be arranged at a perimeter of the device, and is configured for tissue apposition in the aortic arch, wherein the shape is ovale, elongate or patient-configured to the interior of the aortic arch.

The ovale form has an increasing width towards the distal end of the device in some embodiments.

In some embodiments, the delivery device is arranged at an angle with the support member in a longitudinal direction of the device.

In some embodiments, the selectively permeable unit is devised to be repellant to embolic material.

In some embodiments, the selectively permeable unit is stretched over the first support member, such as a sock, in a double layer configuration.

In some embodiments, the protective unit is sized and shaped to extend across an apex of the aortic arch.

In some embodiments, the device has a perimeter adapted to be arranged towards tissue of the aortic arch, wherein a tissue protective unit is provided at least partly at the perimeter of the device. The tissue protective unit may be a cuff that is inflatable via an inflation lumen or self-inflatable; a hollow, porous, spongy, and/or resilient unit; or a soft and/or elastic unit in the form of a coating or surface layer arranged at least along a portion of the perimeter of the protection device.

In some embodiments, the selectively permeable unit is of a rigid, non-elastic material, substantially non-flexible, material, whereby the permeable unit is non-conformable to ostia regions of the side branch vessels.

The device may comprise a plurality of struts extending from the support member and arranged to support the selectively permeable unit in form of a framework. The struts may be resilient.

In some embodiments, the device comprises at least one wing sections shaped to extend a certain distance down into an ascendant and/or descendant aorta from the aortic arch, at an end portion thereof.

In some embodiments, the device comprises a plurality of sub-sections of the protection device arranged as multi-layers, wherein a plurality of peripheral support units and/or sealing units is provided in series.

The selectively permeable unit may comprises a mesh material or fabric comprising a mesh of strands, and/or a hydrophobic material and/or a hydrophobic agent. The selectively permeable unit may be devised to substantially not trap the embolic material in the selectively permeable unit. The selectively permeable unit may be devised to releasably trap at least a part of the embolic material from a blood flow in the aortic arch.

In some embodiments, the selectively permeable unit comprises a first portion devised to extend in a first direction towards a descending aorta of the aortic arch from the connection point, and a second portion devised to extend in a second direction, opposite to the first direction, towards an ascending aorta of the aortic arch from the connection point, when the protection unit is positioned in the aortic arch, in the expanded state.

In some embodiments, the selectively permeable unit is arranged to asymmetrically extend from the connection point in a first direction towards a descending aorta of the aortic arch and in a second direction towards an ascending aorta of the aortic arch, when the protection unit is positioned in the aortic arch, in the expanded state.

In some embodiments, the selectively permeable unit is devised for percutaneous transvascular delivery through one of the aortic side branch vessels to the aortic arch, in a collapsed state.

In some embodiments, the protective device comprises a safety connection for preventing loosening of the device into the descending aorta.

In some embodiments, a distal portion of the device is provided in form of an angled extension, or a nose.

According to another aspect of the invention, a method is provided. The method is a medical procedure. A method of preventing embolic material from entering side branch vessels with a blood flow from an aortic arch of a patient, the method comprising percutaneously introducing a collapsible embolic protection device in a collapsed state into a peripheral blood vessel in fluid communication to a first side branch vessel of the side branch vessels; transvascularly delivering the collapsible embolic protection device in a collapsed state into the aortic arch via the peripheral blood vessel and the first side branch vessel, and through an ostium of the first side branch vessel, while avoiding contact with the ostium, and attached to a transvascular delivery unit at a connection point or region, or an attachment point thereof; expanding a protection unit of the collapsible embolic protection device in the aortic arch, wherein the expanding comprises asymmetrically expanding a first portion of the protection unit and a second portion of the protection unit from the connection point or region, or attachment point, in a first direction towards a descending aorta of the aortic arch and in a second direction towards an ascending aorta of the aortic arch; and thus positioning the protection unit in the aortic arch in the expanded state, and preventing embolic material from passage with a blood flow into a plurality of aortic side branch vessels at the aortic arch by a selectively permeable material of the protection unit.

A second branch vessel, different from the branch vessel through which delivery is made, is protected from embolic material by the embolic protective device. In particular, by access via the left arm and the left subclavian artery, one or more of the left or right carotid artery are effectively protected.

The method may comprises percutaneous transvascular delivery of the embolic protection to the aortic arch through one of the aortic side branch vessels that is different from aortic side branch vessels leading to the head or neck of the patient such as the brachiocephalic artery and the left carotid artery, in a collapsed state.

The method may comprises percutaneous transvascular delivery of the embolic protection through one of the aortic side branch vessels different than the aortic side branch vessels temporary protected by the device when delivered to the aortic arch.

In embodiments of the method, the aortic side branch vessel for the delivery is the left subclavian artery of the patient, for instance directly accessed via a puncture in a vessel of the left arm of the patient.

The method may comprises positioning the device to extend over the ostia of a first, second and third of the side branch vessels, wherein the first side branch vessel is the left subclavian artery, the second side branch vessel is the left common carotid artery, and the third side branch vessel is the brachiocephalic artery.

In an embodiment, the protection unit is delivered off-center by the transvascular delivery unit being connected off-center at the connection point.

In an embodiment, the embolic protective device is attached to an introducer sheet in the subclavian artery such that the embolic protective device is in position in the aortic arch protecting the carotid arteries.

Further embodiments of the invention are defined in the dependent claims, wherein features for the second and subsequent aspects of the invention are as for the first aspect mutatis mutandis.

Embolic material generally ranges from 0.02 mm (20/μm) to 5 mm in particle size or diameter.

Embolic material and consists predominantly of atheromatous fragments dislodged from the aortic wall, but also includes platelet aggregates which form during cardiac surgery, thrombus in general, globules of fat, clumps of bacteria and/or other foreign matter, tumor cells, or any other bits of tissue. These emboli are transported with the blood stream and enter either the cerebral circulation or systemic arterial system. Those entering the cerebral circulation obstruct small arteries and lead to macroscopic or microscopic cerebral infarction, with ensuing neurocognitive dysfunction. Specifically, cerebral embolization contributes significantly to problems such as stroke, lengthy hospital stays, and, in some cases, death. The term "embolic material" used in the context of the present application means material in blood having the aforementioned structural properties and/or effects; broadly, the term refers to any undesired or occluding material in vessels or other body lumen.

A branch vessel is an entirely new vessel branching from a first vessel and typically has a different name.

The present invention addresses the dangers in particular associated with cerebral embolization.

The device is intended for usage during cardiovascular procedures/operations within the field of invasive cardiology or cardiac surgery, where protection against embolization of particles into the head vessels is desired. The device improves patient safety during medical procedures, such as cardiovascular interventions or cardiac operations where the manipulation of the aorta, coronary vessels, bypass grafts, and the heart's valves otherwise can result in embolization of particles into the head vessels causing an ischemic injury to the brain. The medical procedures may be minimally invasive themselves.

The device may be positioned in the aortic arch by using a standard Seldinger technique and fluoroscopy with access through an introducer in the radial- or brachial artery. The protective device is delivered using a catheter that is positioned in the aorta through the subclavian artery. Once the collapsible protective device is delivered/released out of the catheter it expands and can be placed to cover the head vessels working as a "lock", letting through blood but not embolized particles. When the cardiovascular intervention or cardiac operation is over the device is retracted into the catheter again.

Some embodiments of the invention provide for a reliable and safe cerebral embolic protection. Leakage of embolic material to the brain is effectively prevented.

Some embodiments provide for a mechanical protective function of certain tissue or certain organs in the vicinity of the device, when at its position in the body. Some embodiments of the device provide for instance a protection of the aorta side branch vessels' ostia, i.e. the tissue islands of the side branch vessels in the aortic arch, wherein protection means mechanical protection preventing physical access to the ostia from the aorta side, e.g. by surgical tools manipulated in or close to the aortic arch. The tissue islands are protected from mechanical compression by the embolic protection device. Mechanical compression may for instance arise from other devices that are manipulated in the aortic arch when the protection device is positioned therein. Other devices comprise transvascular medical instruments, such as surgical instruments, guidewires, catheters, etc.

Some embodiments provide for a device adapted for delivery via another branch vessel than one of the at least one branch vessel to be protected.

Some embodiments provide for less bulky devices, e.g. by having an attachment point or connection point that is arranged off centre at the embolic protection device.

The off centre position of the embolic protective device offers the possibility to attach it to an introducer sheet. For example if working via an introducer sheet in the subclavian artery the embolic protective device could be in position, protecting the carotid arteries, when carrying out the intervention.

The term "off centre" used in the context of the present application means eccentric, or not arranged or located in a center. The center is e.g. a center of a circular unit, a focal point of an elliptical unit, a point on a center line, such as a longitudinal center line of an elongated unit, etc. A periphery of a unit is located "off centre" as it is arranged at a distance in relation to a center of the unit.

The term "collapsible" used in the context of the present application means that a dimension of a device is reducible to a lesser dimension such that it is arrangeable in a tubular delivery unit, such as a catheter. A collapsible unit is expandable when released or pushed out of the delivery unit. Expandable comprises self expandable, e.g. by a shape memory effect and/or resilient elasticity. A collapsible unit is the re-collapsible for withdrawal into the delivery unit and out of the patient.

Some embodiments provide for a device adapted for delivery via the left arm and the left subclavian artery as an access point.

Using the left subclavian artery as an access point has advantages in certain interventions as it offers a shorter distance and less angulations than when compared to using for example the femoral artery as an access point.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
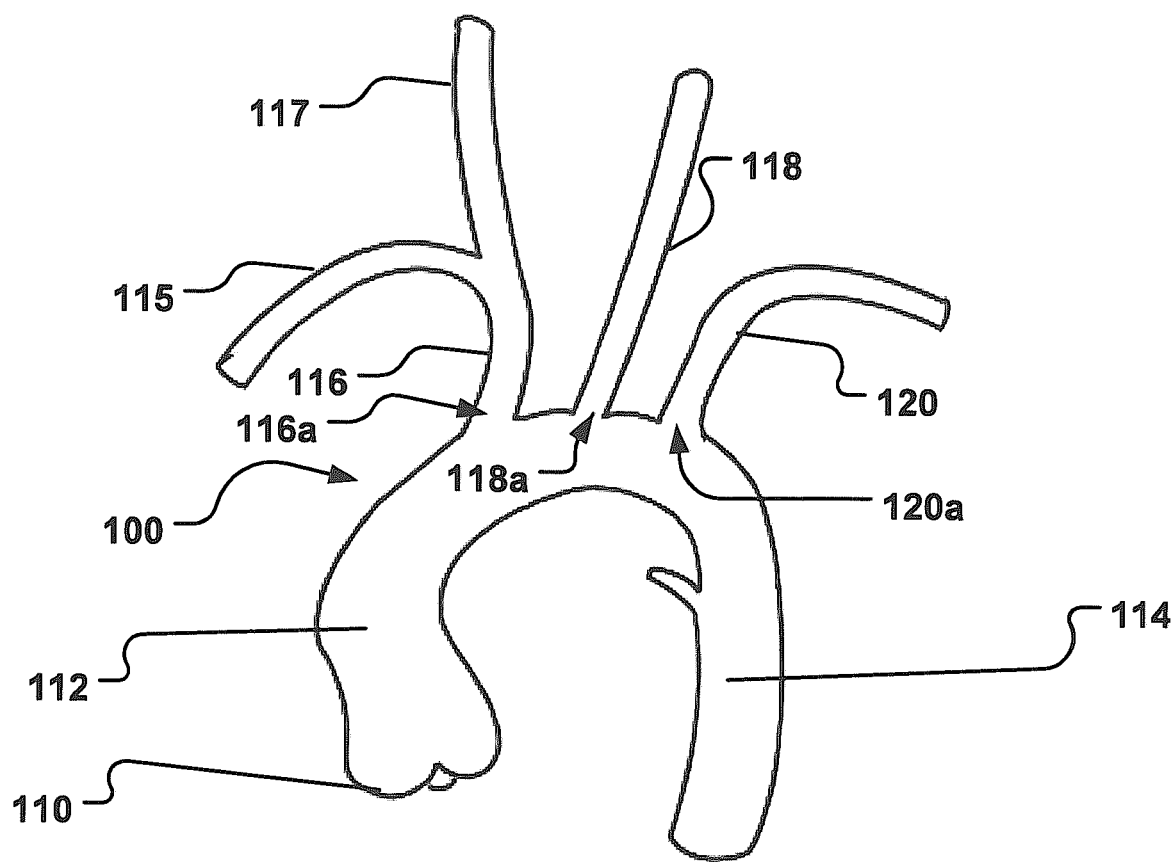
FIG. 1 is a schematic illustration of an aortic arch and side branch vessels.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

In order to get a better understanding of the anatomical situation in which the present invention is carried out, FIG. 1 shows a schematic illustration of an aortic arch 100 and a plurality of side branch vessels, including a third side branch vessel 116, a second side branch vessel 118, and a first side branch vessel 120.

The aortic arch 100 describes a large bend in the ascending aorta 112 after it leaves the heart 110 via the aortic valve. The ascending aorta 112 makes a sweeping, double twisting bend toward the dorsal surface of the body. The twisting and bending ultimately results in a generalized 180-degree bend or arch, namely the aortic arch 100 that transforms into the descending aorta 114. The side branch vessels 116, 118, 120 comprise important arteries that supply oxygenated blood to the neck and head. The side branch vessels 116, 118, 120 have their origin in branches off the aortic arch 100. The opening in the aorta towards a side branch vessel is called ostium.

Normally, three branches of the aorta split off from the trunk of the aortic arch in three separate ostia 116a, 118a, 120a. The third side branch vessel 116 is called the brachiocephalic artery, the second side branch vessel 118 is called the left common carotid artery, and the first side branch vessel 120 is called the left subclavian artery, which usually split from the aortic arch as three separate arterial trunks, arising from different positions on the aortic arch 100. This is illustrated in detail in FIG. 1.

The brachiocephalic artery 116 is the largest diameter branch of the aortic arch and normally gives rise to a bifurcation from which extend the right subclavian artery 115, leading blood e.g. to the right arm, and the right common carotid artery 117 conveying arterial blood towards the neck and head. The left common carotid artery 118 usually branches directly from the aortic arch 100. The common carotid arteries 117, 118 then branch into the external and internal carotid arteries that supply blood to the neck and head regions.

The left and right subclavian arteries 120, 115 ultimately provide the arterial path for blood destined for the vertebral arteries, the internal thoracic arteries, and other vessels that provide oxygenated blood to the thoracic wall, spinal cord, parts of the upper arm, neck, meninges, and the brain.

The spacing of the ostia 116a, 118a, 120a relative each other may vary from patient to patient. It is also not uncommon for one or more of these major arteries to be fused for a time. For instance two of the branches may split off from a common trunk, or the number of branches may be increased to four or more if, for example, the right common carotid artery 117 branches directly from the aortic arch 100 instead of from the brachiocephalic artery 116 at a bifurcation with the right subclavian artery 115.

In embodiments of the invention, a collapsible embolic protection device 200 is provided that is devised for temporary transvascular delivery to an aortic arch 100 of a patient, and temporary positioning in the aortic arch 100. Several embodiments of the device are described below. The devices have a collapsible protection unit 140 for preventing embolic material 150 from entering into at least one of the side branch vessels 116, 118, 120 of the aortic arch 100 in an expanded state thereof when suitably positioned in the aortic arch 100. Preferably at least the left and right carotid arteries 118, 117 are protected from embolic material 150 present in the aortic arch 100.

The protection unit 140 comprises a selectively permeable material or unit 132 adapted to selectively prevent embolic material 150 from passage with a blood flow (symbolic arrows in FIG. 3) into the plurality of aortic side branch vessels 116, 118, 120 at the aortic arch 100. The blood flow into the side branch vessels is substantially not hindered when passing the embolic protective device 200. The protection unit 140 is permanently connected to or attached to a transvascular delivery unit 130 at a connection point or region, or an attachment point 131 provided at the selectively permeable unit 132. The connection point or region may for instance be provided when the protection unit is integral with a support element thereof, and not attached thereto, but transiting from the transvascular delivery unit 130 to the protection unit 140, e.g. at a support member of the protection unit 140, such as described below.

Figure 2:
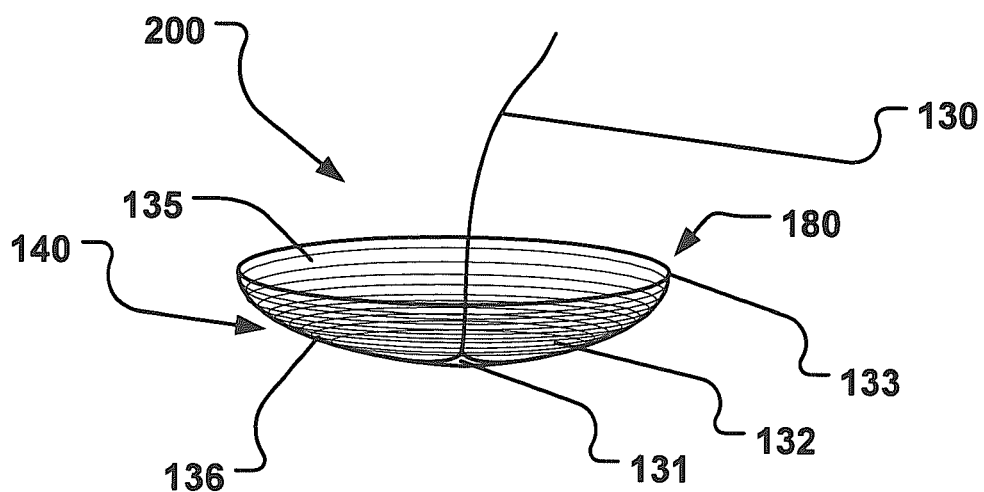
FIG. 2 is a schematic illustration of a protective device attached to a transvascular delivery unit in its expanded configuration.
Figure 3:
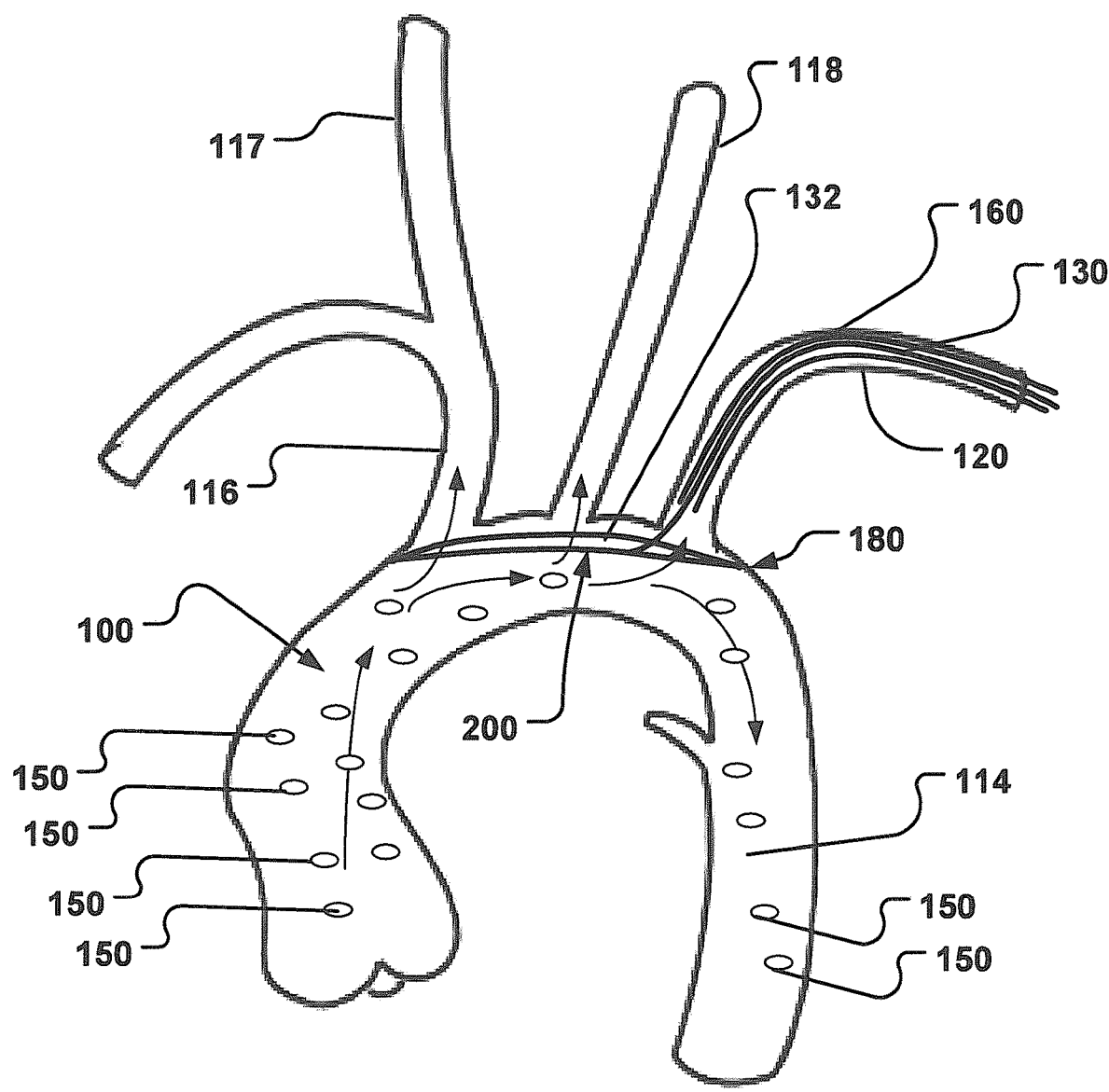
FIG. 3 is a schematic illustration of a protective device attached to a transvascular delivery unit in its expanded configuration deployed in an aortic arch.
Figure 4A:
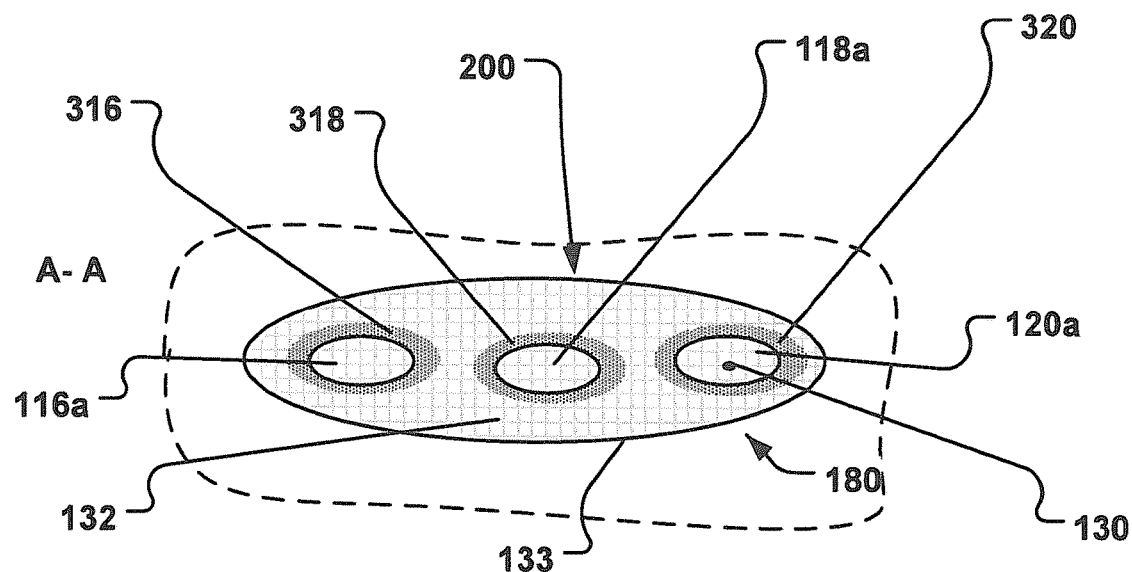
FIGS. 4A and 4B are further detailed illustrations in a view from inside the aortic arch towards the side branch vessel ostia, and a cross sectional view of protective device attached to a transvascular delivery unit in its expanded configuration deployed in the aortic arch.

The attachment point may be arranged centrally at the protection device 200, as illustrated in FIG. 2. Alternatively, the attachment point is in embodiments arranged off-center in relation to a center of the protection device 200, or the selectively permeable material thereof, such as shown in FIG. 3 or 4A. The attachment point may even be provided on the device 200 in a manner that the device is arranged in the aortic arch 100 off-center relative to the ostium through which it is delivered. The attachment point may be arranged such that it is positioned upstream or downstream the delivery ostium in the aortic arch, for instance at a distance from that ostium, e.g. at another ostium, or for instance in the descending aorta when the protective device is delivered in the aortic arch. This is for instance illustrated in FIG. 3, FIG. 4B, or FIG. 6A.

The embolic protection device 200 further comprises a first support member 133 for the protection unit 140 that is at least partly arranged at a periphery 180 of the selectively permeable unit 132. The selectively permeable unit 132 is permeable for blood but impermeable for embolic material. The selectively permeable unit 132 is connected or attached to the first support member 133 by in a suitable manner or by suitable means, such as gluing, welding, stretching over around the periphery, e.g. such as a sock in a double layer, or in a single layer. Alternatively, the selectively permeable unit 132 may be integral with the first support member 133, e.g. by a suitable braiding technique, laser perforation or puncturing of a flat sheet being the selectively permeable unit, etc. The first support member 133 may be provided in form of a wire. The wire may be of circular diameter or flattened for improved tissue friendly apposition. The wire may be integral with the transvascular delivery unit 130, when the latter comprises an elongate wire transiting to the protection unit 140.

In an expanded state of the device 200, the attachment point 131 is enclosed by the first support member 133. Alternatively, the connection or attachment point 131 is arranged at a location being at least one point of the first support member 133. Alternatively, or in addition, the connection point is integral with the first support member 133, see e.g. FIG. 9, 10, or 1.

Figure 5A:
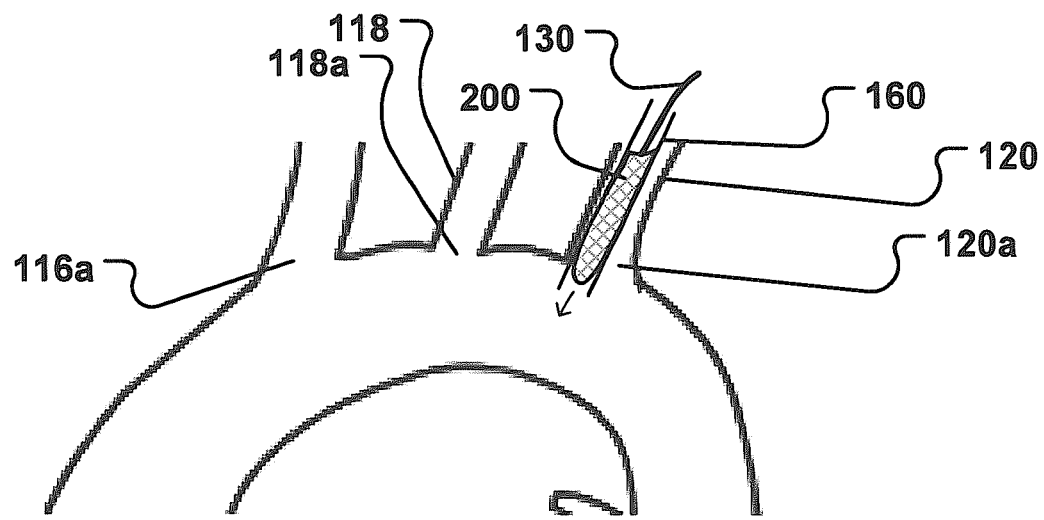
FIGS. 5A to 5C are schematic illustrations of different stages during transvascular delivery of a protective device through a side branch vessel into the aortic arch of a patient.
Figure 5B:
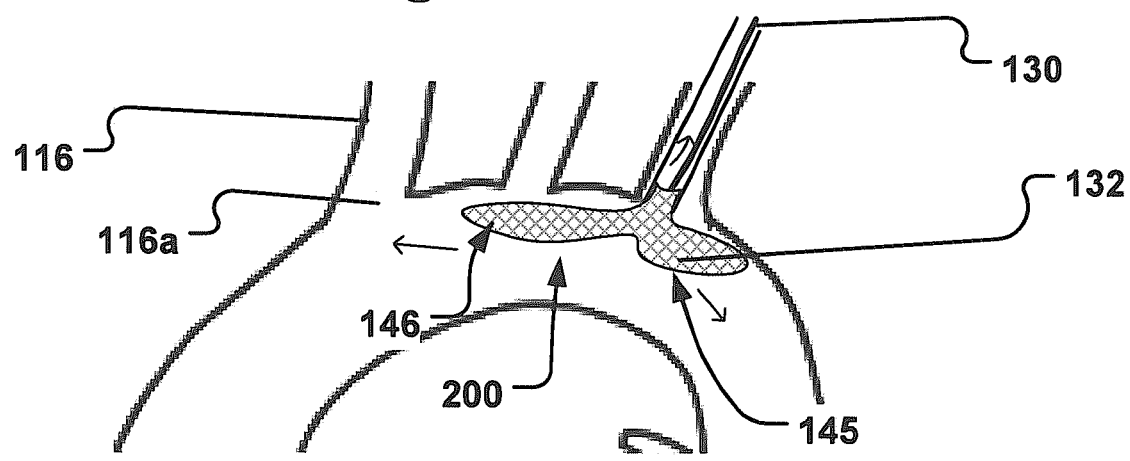
Figure 5C:
Figures 7A, 7B:
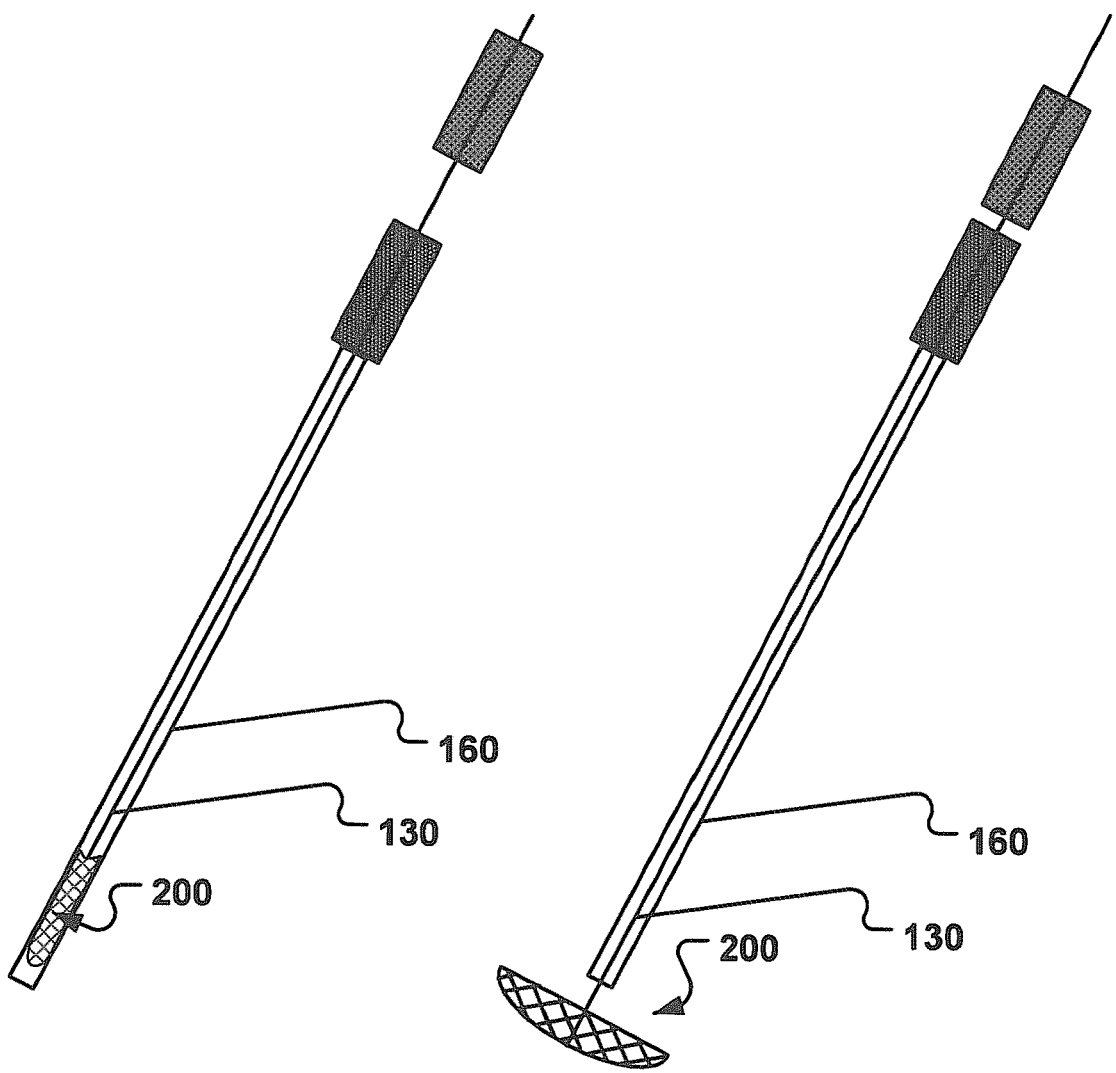
FIGS. 7A and 7B are schematic illustrations of a collapsed and expanded protective device and an attached delivery unit.
Figure 8:
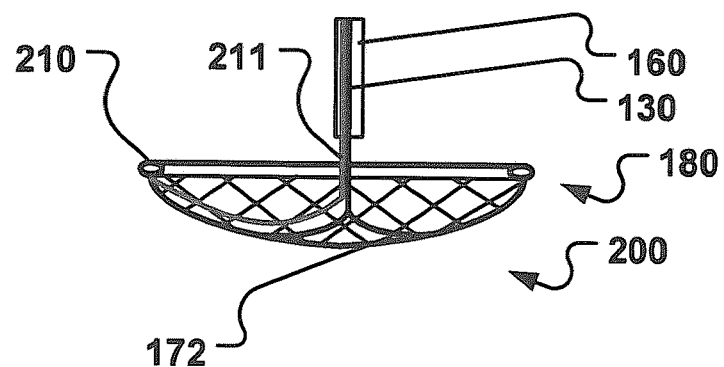
FIG. 8 is a detail of an attachment point of a delivery unit to a protective device comprising a protective cuff.

In some embodiments, the attachment point 131 is arranged in a plane different than that enclosed by the periphery 180 of the selectively permeable unit 132, see e.g. FIG. 5C, 7B or 8. The attachment point 131 is arranged in a plane oriented away from the ostia 116a, 118a, 120a in relation to the periphery 180. The attachment point is for instance provided on a first surface 135 of the selectively permeable unit 132 oriented towards the ostia 116a, 118a, 120a, in the expanded and delivered state of the device 200, see e.g. FIG. 8.

In this manner, delivery through one of the side branch vessels is facilitated. The device 200 may thus reliable be positioned. Leakage of blood and embolic material past the periphery 180 may advantageously be minimized or avoided. Depending on the characteristics of the selectively permeable unit 132, embolic material may be temporary trapped in the selectively permeable unit 132. The selectively permeable unit 132 may comprise a filter material. Alternatively, or in addition, the selectively permeable unit 132 may comprise or be made of a porous material, such as a sintered material, including sintered metal. Alternatively, or in addition, the selectively permeable unit 132 may have characteristics that the embolic material glides or slides along a second surface 136 thereof oriented away from the ostia 116a, 118a, 118a.

In embodiments of the collapsible embolic protection device, the transvascular delivery unit is attached off-center to the selectively permeable material at the attachment point. The attachment point 131 is for instance provided on a different location than the center point of the selectively permeable unit 132 on the first surface 135 thereof, as e.g. illustrated in FIG. 3, in contrast to the illustration of FIG. 2.

The first support member 133 is shaped to apposition to tissue of a vessel wall portion of the aortic arch 100. The first support member 133 may releasably engage with the tissue of the vessel wall portion. The first support member 133 is formed to encircle the plurality of ostia 116a, 118a, 120a of the aortic side branch vessels 116, 118, 120 inside the aortic arch 100, and at a distance to the ostia 116a, 118a, 120a. In this manner the selectively permeable unit 132 is arranged to separate a first fluid volume of the aortic side branch vessels 116, 118, 120 from a second fluid volume in the aortic arch 100 when the protection unit 140 is positioned in the aortic arch 100, as illustrated in FIG. 3.

Figure 4B:
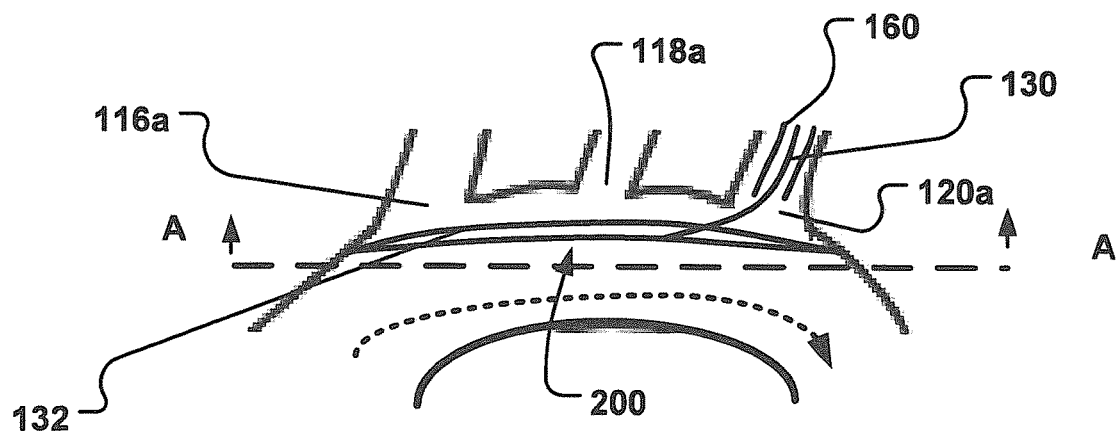

FIGS. 4A and 4B are further detailed illustrations in a view from inside the aortic arch towards the side branch vessel ostia, and a cross sectional view of protective device attached to a transvascular delivery unit in its expanded configuration deployed in the aortic arch. It can be seen that the device 200 is arranged such that the support unit 133 appositions the vessel tissue of the aortic arch, and encloses the ostia 116a, 118a, 120a of the side branch vessels 116, 118, 120 at a distance thereto. The selectively permeable unit 132 is arranged in the aortic arch 100, also at a distance from the ostia 116a, 118a, 120a of the side branch vessels 116, 118, 120. The device 200 is thus arranged in a flow direction of blood in the aortic arch, as indicated by the dotted arrow in FIG. 4B. The expanded device extends generally longitudinally along the aorta at the apex of the aortic arch 100 and at the inside thereof.

Regions of accumulated plaque 316, 318, 320 at the ostia 116a, 118a, 120a are not contacted by the device 200. Thus the plaque rests at its place and it not released. The distal end of the catheter 160 of the transvascular delivery unit, from which the protection unit 200 is released, may be positioned further into the aortic arch 100 as illustrated in FIG. 4B, and thus further improve the protection of regions of accumulated plaque 320 at the delivery vessel 320, due to its relative stiffness of the provided catheter sheath.

Figure 13:
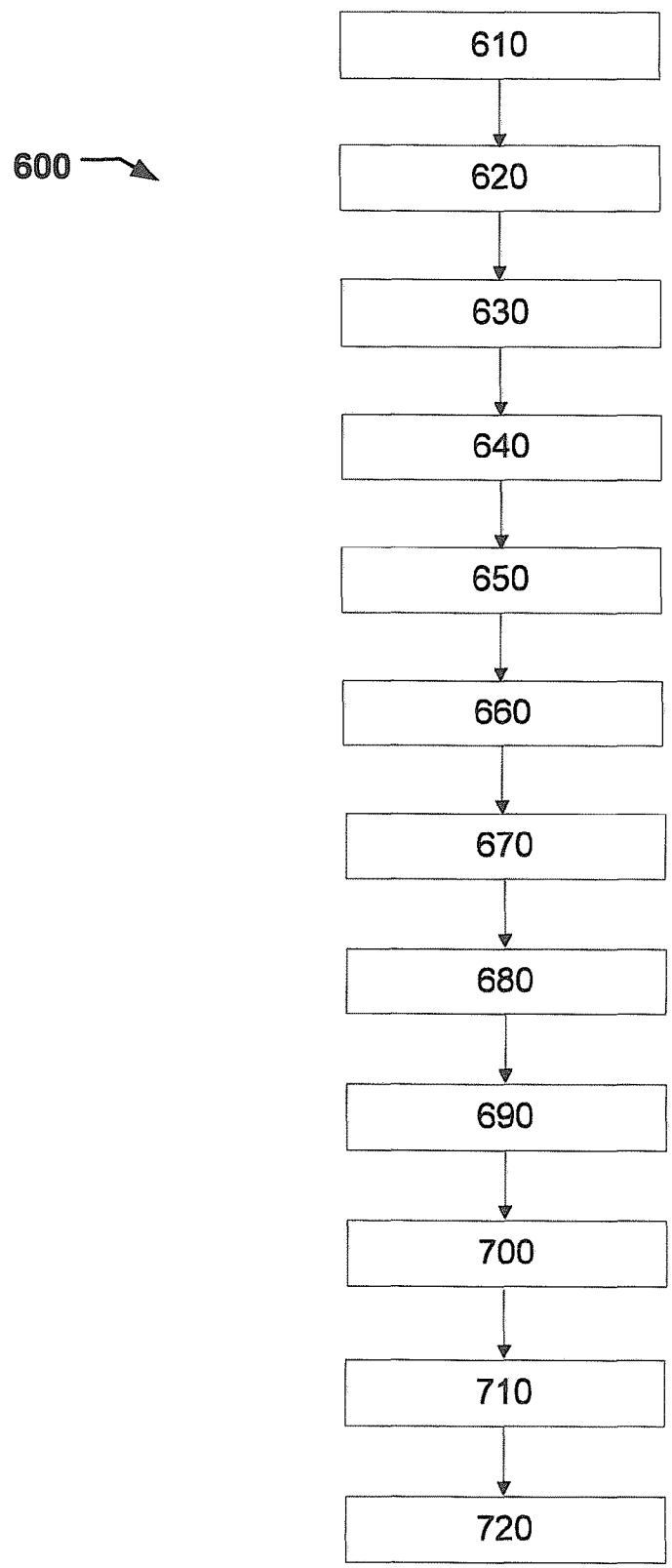
FIG. 13 is a flow chart illustrating a medical procedure.

With reference to FIG. 13, as well as FIGS. 5A-5C and 6A-6C a flow chart illustrating a medical procedure of positioning the device 200 in the aortic arch is now described in more detail, before further embodiments of the device 200 are described thereafter.

FIGS. 5A to 5C are schematic illustrations of different stages during transvascular delivery of a protective device 200 through a side branch vessel into the aortic arch 100 of a patient.

In the embodied method 600, the device 200 is positioned in the aortic arch 100 by using a standard Seldinger technique and fluoroscopy with access through an introducer in the left radial artery. The protective device 200 is delivered using a catheter that is positioned in the aorta through the left subclavian artery. Once the collapsible protective device is delivered/released out of the catheter it expands and is placed to cover the left and right carotid arteries, letting through blood but not embolized particles. When the cardiovascular intervention or cardiac operation is over the device is retracted into the catheter again.

In the method 600 of preventing embolic material from entering side branch vessels with a blood flow from an aortic arch of a patient, a collapsible embolic protection device 200 is percutaneously introduced in a collapsed state into a peripheral blood vessel, as illustrated by step 610. This is schematically illustrated in FIG. 5A. The peripheral blood vessel is in downstream fluid communication to the first side branch vessel 120 of the plurality of side branch vessels of the aortic arch, namely the left subclavian artery 120. The first side branch vessel 120 is oriented downstream the second and third branch vessel 118, 116, seen in the direction of blood flow in the aortic arch. This delivery access point via the first side branch vessel downstream the branch vessel(s) to be protected by the device 200 provides a major advantage as iatrogenic debris will not be washed towards the brain of the patient.

The collapsible embolic protection device 200 is transvascularly delivered in a collapsed state into the aortic arch 100 via the peripheral blood vessel and the first side branch vessel 120, as illustrated by step 620. For this purpose, the device 200 is collapsed into a delivery catheter 160 and introduced through the latter to the deployment site inside the aortic arch 100. The delivery path comprises the ostium 120a of the first side branch vessel 120. Contact with the ostium 120a and surrounding tissue is avoided, in order to not release any plaque or other debris therefrom. However, in case any debris should be created by unintended contact with the ostium 120a of the left subclavian artery 120, this would be washed away from the carotid arteries with the blood stream in the aorta or into the first side branch vessel, which would not have the risk of ischemic cerebral injury or major stroke as debris washed into the carotid arteries.

The device 200 is attached to a transvascular delivery unit 130, such as a pusher or wire, at an attachment point thereof. As illustrated in FIG. 5B and further FIG. 5C, the embolic protection unit 200 of the collapsible embolic protection device is expanded in the aortic arch, which is illustrated by step 630.

In the illustrated embodiment, the expanding comprises asymmetrically expanding a first portion 145 of the protection unit and a second portion 146 of the protection unit from the attachment point 131. The first portion 145 is expanded in a first direction towards the descending aorta 114 of the aortic arch 100. The second portion 146 is expanded in a second direction towards the ascending aorta 112 of the aortic arch 100. The asymmetric arrangement facilitates the positioning of the device 200 from the delivery vessel 120 in relation to the other side branch vessels 116, 118 to be protected. This method stage is illustrated by step 640.

Alternative devices may only be expanded in the direction of the second and third branch vessels, providing a diverter for embolic material.

The positioning the protection unit 200 in the aortic arch 100 comprises appositioning a first support member 133 of the selectively permeable unit 132 of the protective unit 200 to tissue of a vessel wall portion of the aortic arch 100, as illustrated by step 650. The first support member 133 of the protection unit 200 is at least partly arranged at a periphery 180 of the selectively permeable unit 132 of the protection unit. The first support member 133 is enclosing, in an expanded state of the device, the attachment point 131 by the first support member 133.

The method comprises encircling a plurality of ostia 116a, 118a, 120a of the aortic side branch vessels 116, 118, 120 in the aortic arch 100 with the first support member 133, and positioning the protective unit 200 at a distance to the ostia 116a, 118a, 120a. This method stage is illustrated by step 660. Alternatively, only the ostia 116a, 118a are protected.

Figure 6A:
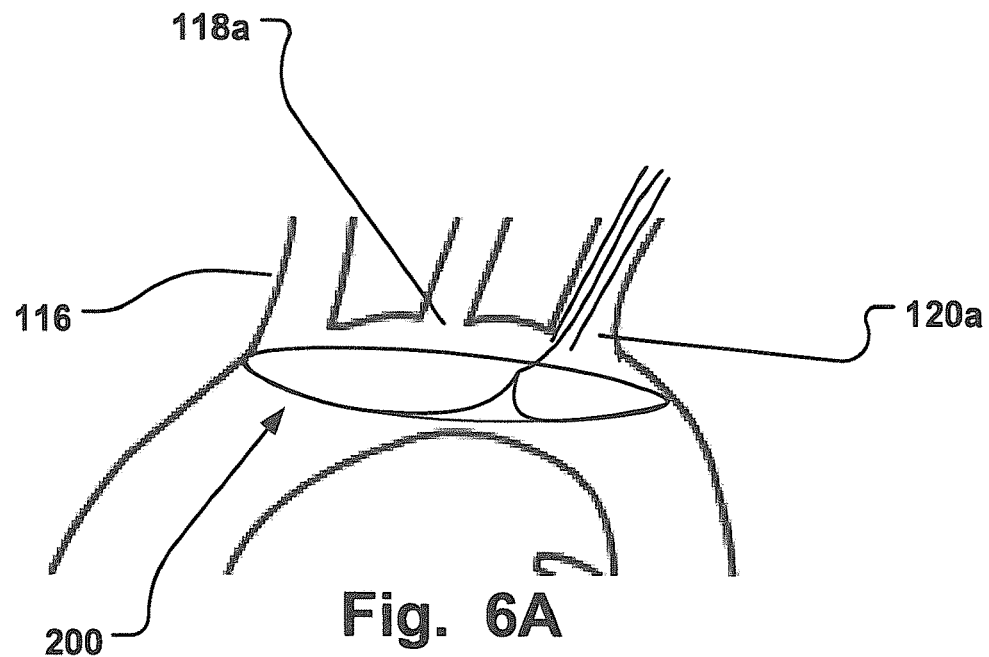
FIGS. 6A to 6C are schematic illustrations of different stages during withdrawal a protective device through a side branch vessel from the aortic arch of a patient.

Thus, the protection unit 200 is positioned in the aortic arch 100 in the expanded state thereof, as illustrated in FIG. 6A and in method step 670. Embolic material 150 is effectively prevented from passage with a blood flow into a plurality of aortic side branch vessels 116, 118, 120 at the aortic arch 100 by the selectively permeable material of the protection unit 200, see method step 680.

The method thus provides for concurrently separating a first fluid volume of the aortic side branch vessels from a second fluid volume in the aortic arch when the protection unit 200 is positioned in the aortic arch 100.

The method may comprise drawing the expanded protection unit 200 into a direction opposite a delivery direction, and thus tensioning and tightening against a vessel tissue portion of the aortic arch 100 encircling the ostia of the side branch vessels. This embodied method stage is illustrated by step 690.

The tightening and sealing around the periphery 180 of the protection unit 200 is further supported by blood pressure and blood flow in the aortic arch pressing the protection unit against the vessel tissue portion.

The positioning of the protection unit 200 in the aortic arch may comprise releasably engaging the protection unit 200 with tissue of a vessel wall portion of the aortic arch, see step 700. This may be accomplished by the aforementioned drawing the delivery unit 130 against the delivery direction. Thus a further improver leakage tight prevention of passage of embolic material into the side branch vessels is accomplished. The tissue of the aorta vessel is not damaged and trauma thereof is effectively prevented. The first support member 133 may for instance have a rounded diameter, and/or be of a soft exterior material or comprise a suitable coating for even further improving these characteristics. The first support member 133 may be provided in form of a peripheral collar or cuff that is atraumatically protecting the vessel tissue of the aorta wall.

The method comprises arranging the permeable unit at a distance from ostia of the side branch vessels into the aortic arch. The arranging comprises for instance not contacting ostia of the side branch vessels into the aortic arch.

Triggering of release of embolic material from the ostia, such as debris, is thus effectively prevented by covering all side branch vessels, and not contacting the ostia of the side branch vessels into the aortic arch.

Prevention of embolic material from entering side branch vessels with a blood flow from an aortic arch of a patient may comprise directing embolic material past the ostia of the aortic side branch vessels of the aortic arch, along a surface of the selectively permeable unit devised to be oriented away from ostia of the aortic side branch vessels of the aortic arch, when the protection unit is positioned in the aortic arch, in the expanded state.

Figure 6B:
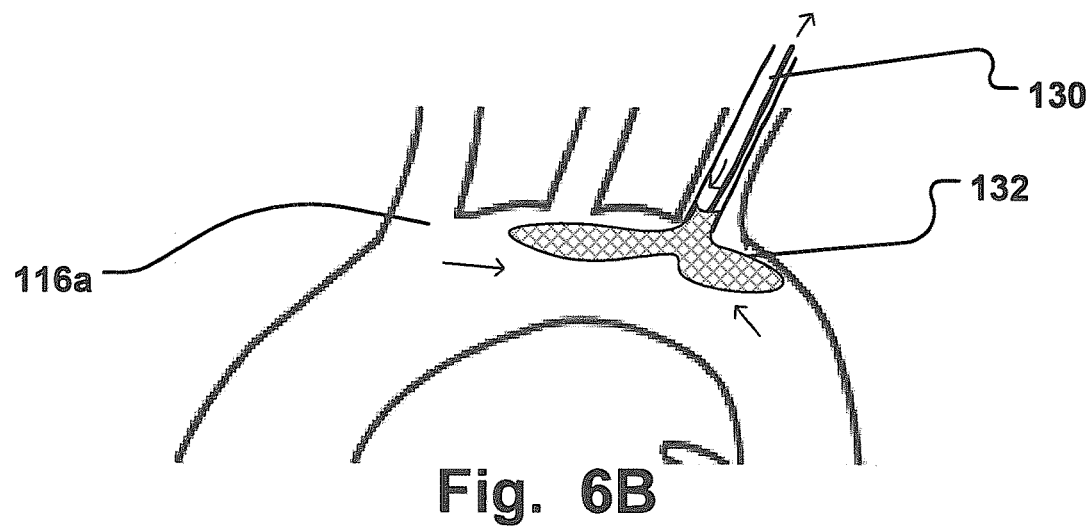
Figure 6C:
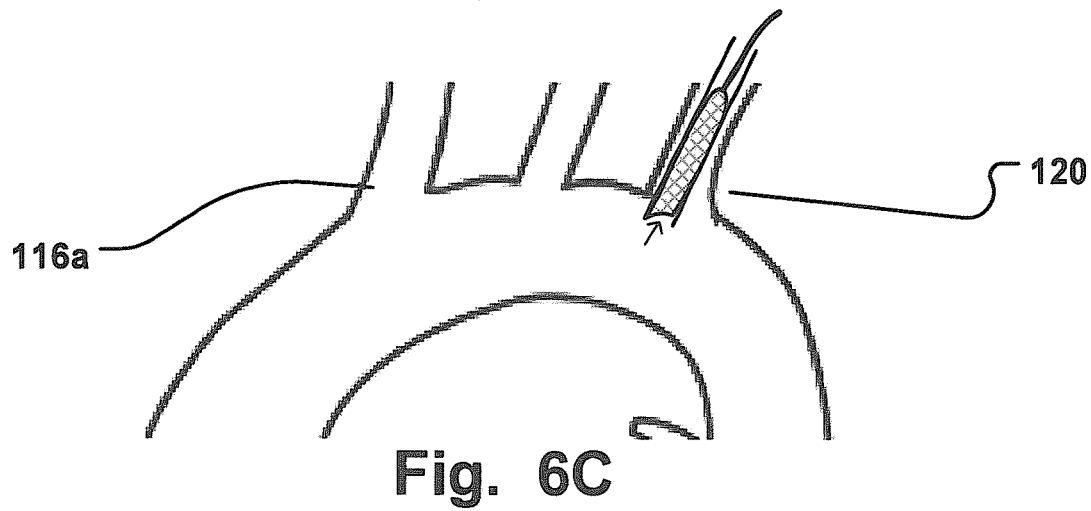

FIGS. 6A to 6C are schematic illustrations of different stages during withdrawal a protective device through a side branch vessel from the aortic arch of a patient.

Extracting the protection device is done by means of the transvascular delivery unit after a temporary placement of the protection unit for the preventing embolic material from entering side branch vessels.

As illustrated in FIGS. 6B and 6C, the extracting comprises releasing the protection unit 200 from engagement with the vessel tissue portion of the aortic arch 100 by pushing the transvascular delivery unit 130 in delivery direction, see step 710.

Embolic material trapped in the protection unit 200 may be released or flushed into a corporeal blood flow towards the descending aorta 114 from the aortic arch 100, before collapsing the protection unit into the sheath.

Furthermore, extraction continues with sliding the sheath of the catheter 160 over the protection unit for collapsing the protection unit into the sheath. Then the collapsible embolic protection device is withdrawn in the sheath through the first side branch vessel 120 and the peripheral blood vessel out of the patient, see step 720.

The collapsible embolic protection device used in the method is in embodiments a device of embodiments as described herein.

FIGS. 7A and 7B are schematic illustrations of a collapsed and expanded protective device and an attached delivery unit.

FIG. 8 is a detail of an attachment point of a delivery unit to a protective device 200. In the illustrated embodiment, the attachment point comprises two arms 171, 172. This embodiment has improved directional stability facilitating positioning in the aortic arch 100. The two arms 171, 172 may also be arranged off-center or asymmetrically. The arms may have the function of supporting struts for the selectively permeable unit of the protection device.

The attachment point of embodiments of the protection device is in some embodiments provided on a surface of the selectively permeable unit 132 devised to be oriented towards the aortic side branch vessels 116, 118, 120 from inside the aortic arch 100 and at a distance from the ostia 116a, 118a, 120a, when the protection unit is positioned in the aortic arch. This is for instance illustrated in FIGS. 3, 4B, 6A.

A tissue protective unit may be comprised in embodiments of the protection device, such as shown in FIG. 8. The tissue protective unit is provided at the perimeter of the protection device, arranged for apposition to tissue of the aortic arch. In FIG. 8 the tissue protective unit is illustrated as a cuff 210 inflatable via an inflation lumen 211. The cuff 210 may also be self-inflatable. The cuff 210 may for instance be made of GoreTex® material. When inflated, the cuff 210 provides a protective cushion for particular tissue friendly apposition to the inner aortic arch wall. Even when the cuff 210 is not inflated it provides a certain degree of tissue protection, as it is hollow. In other embodiments, the tissue protective unit may be a soft and/or elastic material in the form of a coating or surface layer of the perimeter of the protection device. The tissue protective unit may be hollow, porous, spongy, and/or resilient. The tissue protective unit may be made of a swellable material that swells when in contact with blood. Such swellable materials are for instance swellable polymers, such as disclosed in PCT/EP2007/061116, which is incorporated by reference in its entirety herein for all purposes. The degree of swelling is suitably chosen to provide the protective cushioning effect. Such devices, or devices with inflatable cuffs, are advantageously delivered in a compact state.

Thanks to the tissue protective unit the protection device is advantageously leak tight, without damaging the aorta wall, during delivery thereof or when in position in the aortic arch 100.

The selectively permeable unit 132, and thus the protective unit 200 is non-tubular, extending substantially planar in the expanded state. The substantially planar shape includes a flat cupped, inverted umbrella, mushroom, or parachute shapes, as shown in the Figures.

"Flat" in this context means that the thickness of the device 200 is substantially smaller than the longitudinal extension thereof. Moreover, "flat" means such dimensions perpendicular to the longitudinal extension of the protective material, that blood flow through the aortic arch is not hindered by the protective device 200.

The perimeter of the device 200 is configured for tissue apposition in the aortic arch. The shape of the perimeter may be circular, oval, elongate, or even patient-configured adapted to the specific anatomical situation of the patient to be protected by the protective device. Patient-configured devices may be based on data derived from image modalities like CT, MR or Ultrasound.

The device may thus be provided in various longitudinal and transversal extensions, and symmetries. The device may be adapted to the shape of the side branch vessel ostia, see e.g. FIG. 4A or 5B.

Wing sections of the protective device may be shaped to extend a certain distance down into the ascendant and/or descendant aorta in order to further improve stability and/or sealing efficiency at the periphery 180 of the protection device 200. Wing sections are e.g. illustrated in FIGS. 12A and 12B.

A plurality of sub-sections of the protection device may be arranged as multi-layers inside each other. In this manner a plurality of peripheral support units and/or sealing units may be provided in series, in order to further improve stability and/or sealing efficiency at the periphery 180 of the protection device 200.

In an embodiment the selectively permeable unit is non-tubular, extending substantially planar, which peripheral edge is formed by the first support member 133. The first side of the device 200 is devised to be oriented towards the aortic side branch vessels from inside the aortic arch when the protection unit is positioned in the aortic arch, in the expanded state.

The selectively permeable unit 132 is devised to be arranged at a distance from ostia of the aortic side branch vessels of the aortic arch, when the protection unit 200 is positioned in the aortic arch 100, in the expanded state.

The selectively permeable unit 132 is in some embodiments a rigid, non-elastic material, substantially non-flexible, material, which is non-conformable to ostia of the side branch vessels. Alternatively, or in addition, the support frame of the periphery of the device 200 may provide this rigidity to the device. The selectively permeable unit 132 may be stretched by the support frame in the expanded state of the device 200.

Thus, a mechanical protective function of certain tissue or certain organs in the vicinity of the device, is provided, when the device is at its position in the body. A protection of the aorta side branch vessels' ostia, i.e. the tissue islands of the side branch vessels in the aortic arch is provided. The tissue islands are protected from mechanical compression by means of the protection device. Mechanical compression may for instance arise from other devices that are manipulated in the aortic arch when the protection device is positioned therein. Other devices comprise transvascular medical instruments, such as surgical instruments, guide-wires, catheters, balloons, filters, ablation instruments, intracardiac electrodes, etc.

As the protection device lies like a cover or lid (planar or in an inverted flat umbrella/mushroom/parachute shape) over the ostia, at a distance there from, a certain movement towards the ostia due to mechanical pressure from inside the aorta arch is permitted by the protective device.

The protective device may comprise struts across which the selectively permeable material of the unit 132 is arranged. The struts are configured to provide a counter force, such that the selectively permeable unit resiliently returns to an initial position upon a mechanical compression. A plurality of struts may be arranged like struts supporting fabric of an umbrella. The struts may be of a resilient material.

In case of the protection device being made of a heat set braiding, the struts may be implemented in from of thicker wires in the braiding. The remaining braiding may be made of thinner wires and thus provide the selectively permeability of the selectively permeable unit.

The struts keep up and support the selectively permeable material of unit 132.

The struts may be implemented as a plurality of arms 171, 172. The struts are provided as a protective framework for the selectively permeable unit of the protection device.

In an embodiment the selectively permeable unit 132 is a mesh material comprising a mesh of strands. The strands may be of a metallic material, such as stainless steel or Nitinol. Alternatively, or in addition, at least some of the strands may be made of a polymeric material, such as a shape memory polymer.

The mesh of strands forming the protection device may be made of a heat set braiding. Here, the expanded configuration of the device is set. The collapsed device returns to the heat set shape upon delivery. This may be based on an elastic return or a shape memory effect. A manufacturing method that may be modified for protection devices according to the invention, is disclosed in WO9742878A1 and WO9912478A1 of AGA Medical Corporation, which are incorporated by reference in their entirety herein for all purposes. A fabric of resilient metal fabric material is brought to a desired expanded configuration by a mould in a heat setting process. The mould has a shape corresponding to the shape of the protection device in its expanded shape, e.g. the planar shape, or the flat parachute, mushroom, or umbrella shape described herein.

The metal fabric is formed from a plurality of metal strands and is heat treated within the mold in order to substantially set the desired shape of the device. The medical device may include a fastener for attaching to the end of a guide wire or delivery catheter. The shape of the medical device may be formed such that the fastener is attached to the metal fabric within a recess formed in the shape of the medical device.

The device is capable of assuming both an expanded configuration and a collapsed configuration. Once expelled out of a delivery catheter the device returns to its expanded configuration, e.g. in either a planar shape, or a generally flat umbrella-shaped configuration, a generally flat mushroom-shaped configuration, or a generally flat parachute-shaped configuration.

The protective device may be made of plural layers of fabric, such as disclosed in WO07149107A1 of AGA Medical Corporation, which is incorporated by reference in its entirety herein for all purposes. The collapsible medical protection device is shaped from plural layers of a heattreatable metal fabric. Each of the fabric layers is formed from a plurality of metal strands and the assembly is heat-treated within a mold in order to substantially set a desired shape of the device. By incorporating plural layers in the thus-formed medical device, the ability of the device to securely be selectively permeable and mechanically protective is significantly improved.

The strands of the braiding of the protective device is for instance made of NiTinol. NiTinol is a superelastic material ensuring that the compressed device reliable returns to its heats set shape when released from the delivery catheter.

A protective framework may be implemented in from of thicker wires provided within the braiding. The protective framework may be implemented in from of a separate layer of a multi-layer braided structure.

The braiding may has rounded edges at the periphery 180, similar to that shown in FIG. 8. Thus, the braided fabric has edges that are provided as tissue protection units, adapted to be appositioned to the aortic wall tissue without damaging the latter. Alternatively, the braid may have a support frame, e.g. shown in FIG. 10A or 11.

The selectively permeable unit 132 can comprise a hydrophobic material, or comprises a hydrophobic agent, or be made of such a material. This is particularly advantageous to prevent trapping of embolic material in the selectively permeable unit 132.

The selectively permeable unit 132 may be devised to substantially not trap the embolic material in the selectively permeable unit.

Alternatively, or in addition, the selectively permeable unit 132 is devised to releasably trap at least a part of the embolic material 150 from the blood flow in the aortic arch 100. The embolic material may e.g. be trapped in pores or a filter structure of the permeable unit 132.

Alternatively, or in addition, the selectively permeable unit 132 is devised to be repellant to embolic material. Thus, embolic material glides of the selectively permeable unit 132 when the protection device 200 is positioned inside the aortic arch. Such a material is e.g. polytetrafluoroethylene PTFE, commercially available as Goretex®.

The selectively permeable unit 132 comprises a first portion devised to extend in a first direction towards a descending aorta of the aortic arch from the attachment point, and a second portion devised to extend in a second direction, opposite to the first direction, towards the ascending aorta of the aortic arch from the attachment point, when the protection unit is positioned in the aortic arch, in the expanded state. The first and second portions may have different longitudinal extensions.

In embodiments, the selectively permeable unit is arranged to asymmetrically extend from the attachment point in a first direction towards a descending aorta of the aortic arch and in a second direction towards an ascending aorta of the aortic arch, when the protection unit is positioned in the aortic arch, in the expanded state.

Further, the selectively permeable unit is devised for percutaneous transvascular delivery through one of the aortic side branch vessels to the aortic arch, in a collapsed state.

The protective device may comprise an additional safety connection in order to prevent loosening of the device into the descending aorta 114. The safety connection may comprise a safety wire, thread, tether, string, strand, or similar. The safety connection may be attached to the delivery unit or extend all the way through the sheath of the catheter.

In practical implementations, the device has a substantially oval form, approximately 6-10 cm in the longitudinal direction and approximately 3-6 cm in the transversal direction. Wings, or multi-layer structures, as described above, may be provided in addition.

A mesh size or pore size of a material of the selectively permeable unit 132 may be in the range of 20 µm to 100 µm, such as 30-90 µm or 60-80 µm. In this manner embolic material is effectively hindered from passing into the side branch vessels, whereas a passage of blood is not substantially hindered. However, as explained above, trapping of embolic particles, i.e. a collection and accumulation thereof, is primarily not provided by the selectively permeable unit 132.

The selectively material may be manufactured from a flat sheet of material, such as PTFE, which is perforated with holes of suitable diameter to provide the permeability for blood. The holes are provided in a sufficient number to not hinder blood flow across the material, while providing the embolic protection. A schematic illustration is given in FIG. 10A showing permeable material 132 in form of such a flat sheet material. Here, a GoreTex® membrane was laser perforated to the desired permeability.

Figure 9:
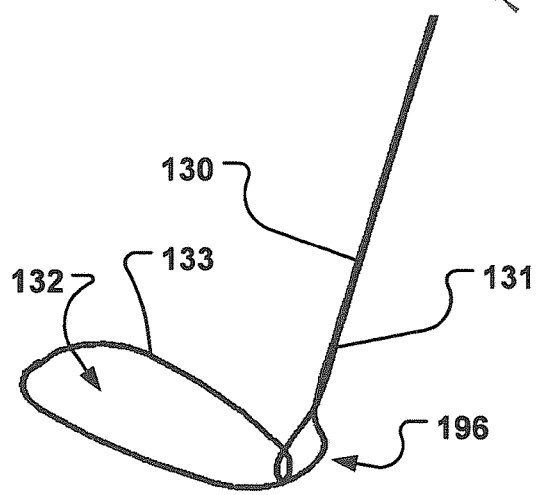
FIG. 9 is a perspective view of another embodiment.

FIG. 9 is a perspective view of another embodiment having a support member 133 in a generally oval configuration. The support member 133 is made of a single wire suitably brought into shape by bending. FIG. 9 illustrates the expanded configuration of the protective device. Two branches of the wire cross each other at a crossing 196 towards the delivery unit 130. The wires are joined at attachment point 131, e.g. by clamping, welding, gluing. Thus, the delivery device is arranged at an angle with the support member 133 in the longitudinal direction of the device 200. This configuration provides for specifically easy introduction into the aortic arch via the left subclavian artery. The angled configuration provides for improved leak protection as it is facilitated to provide a force onto the device towards the aortic wall from the delivery unit 130. The crossing 196 provides for a certain resiliency or flexibility out of the longitudinal direction of the device.

Figure 10C:
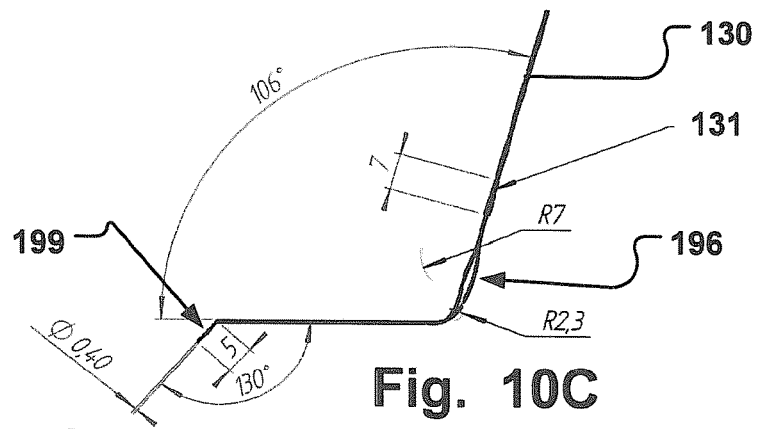
FIGS. 10A-C are a perspective view, a plan view and a lateral view of another embodiment.
Figure 10A:
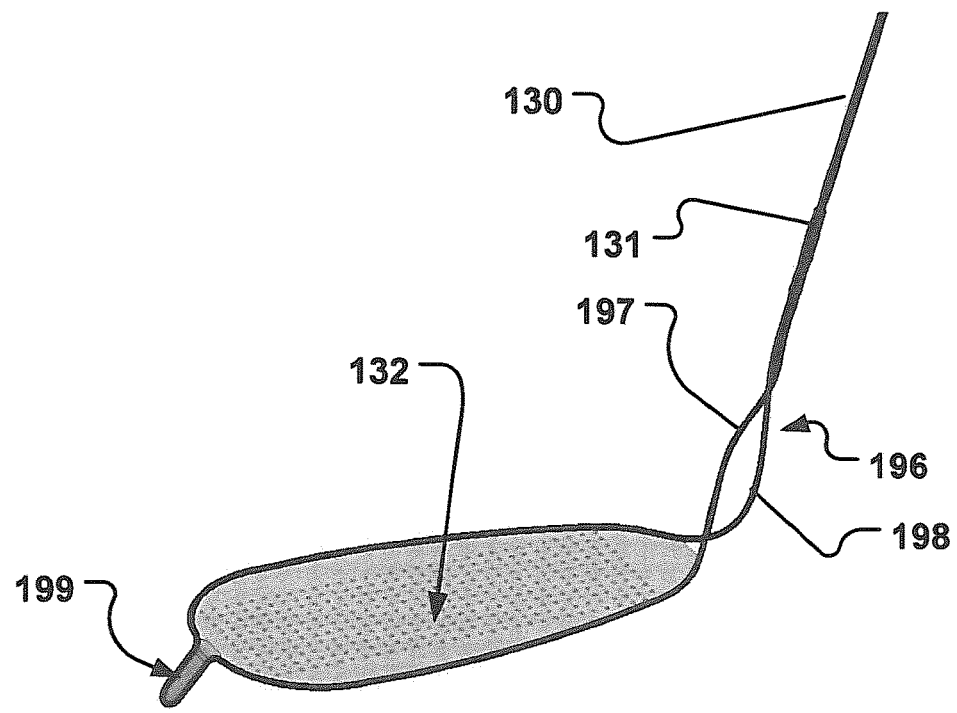
Figure 10B:
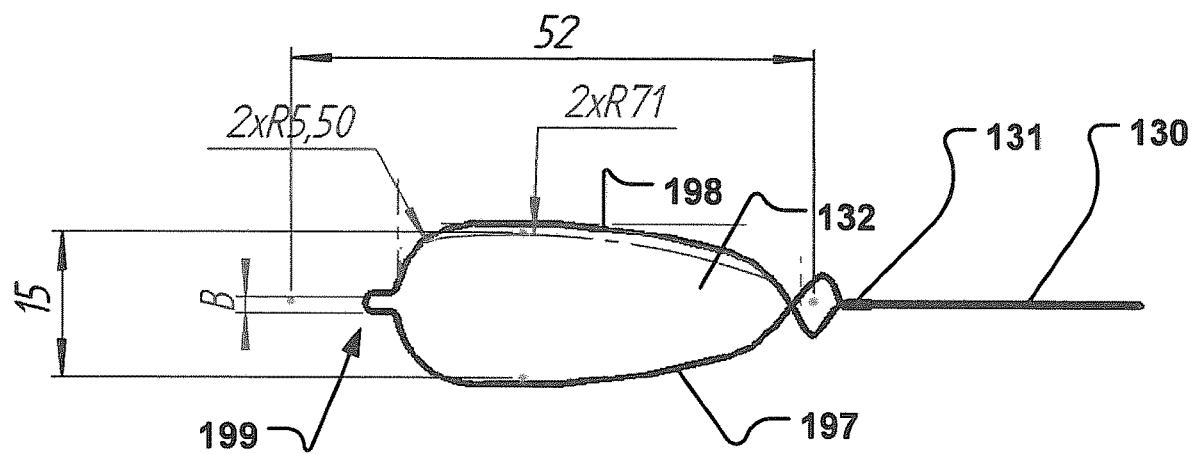

FIGS. 10A-C are a perspective view, a plan view and a lateral view of another embodiment of the device 200. The measurement units in millimeters in FIGS. 10B and 10C are solely given as an example and are not to be interpreted as limiting the invention in any way. However, typical dimensions can be seen in the FIGS. for a specific embodiment.

The device illustrated in FIGS. 10A-C is also angled (here 106°) and has a crossing 196 of a wire of the support member 133. The wire has a first branch 197 and a second branch 198. The ovale form has an increasing width towards the distal end of the device. This shape allows for an improved retraction when retracting the device back into the delivery catheter.

At the distal end of the device, a tongue 199 is arranged. The tongue 199 is made by suitably bending the wire of the support member 133. The tongue has a width B. The tongue 199 facilitates introduction of the device into the delivery catheter by bending the two branches 197, 198 towards each other while pushing the distal end into a proximal catheter lumen opening. The width B is preferably as large as, or smaller as, the inner diameter of the lumen of the catheter. Thus, the tongue 199 is easily introduced into the catheter and the remaining device is pushed into the catheter in an advantageous manner.

The tongue 199 further is arranged at an angle deviating longitudinally from the protection plane of the permeable unit 132 extending between the expanded lateral branches 197, 198, see FIGS. 10A, and 10C. This angled arrangement provides for the tongue 199 to be arranged in the aortic arch in smooth apposition to the vessel wall thereof, without damaging the latter.

In alternative embodiments such a tongue may be attached to the distal end as a separate element.

Figure 11:
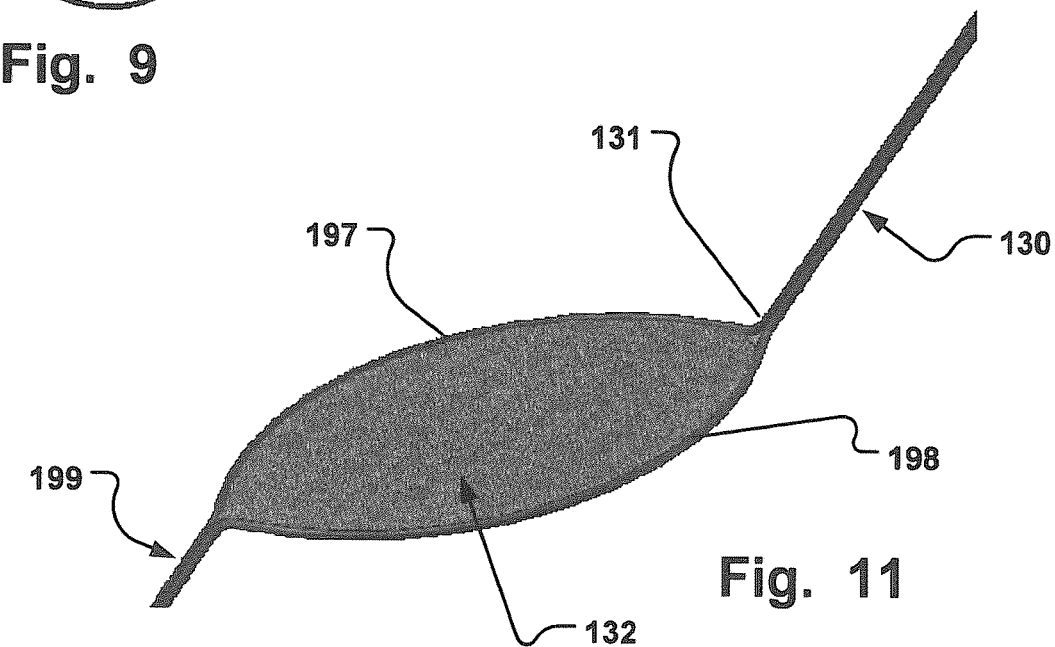
FIG. 11 is a perspective view of another embodiment.

FIG. 11 is a perspective view of another embodiment made of two wires 197, 198. The attachment point 131 is integral with the device. The two wires are affixed to each other at the proximal portion to constitute the delivery device 130 as a double wire. The two wires may be soldered, welded, press-fit, or attached to each other at the proximal portion and the distal portion of the device by other suitable means. Manufacturing of this type of device is particularly advantageous, as it is made time and cost efficiently. The distal portion of the device is provided in form of an angled extension or nose 199. The selectively permeable unit 132 is arranged substantially planar between the lateral wires 197, 198 extending between the attachment point 131 and the nose 199.

A typical duration of use of the device is approximately one hour.

A kit comprises such a collapsible embolic protection device and a transvascular delivery unit adapted for delivery of the collapsible embolic protection device through a side branch vessel of the aortic arch into the aortic arch.

In order to prevent debris from the ostium (120a in the exemplary Figures) that perhaps, despite all caution, is released during the placement of device 200, to reach the brain, a particle trap or filter may be arranged proximally on the delivery unit, in combination to the latter. Such a trap or filter may be provided in a separate lumen of the catheter for release in the delivery vessel upstream the ostium of delivery to the aortic arch 100. The trap or filter may for instance be a vascular filter for positioning in a lumen of the type as disclosed in WO 2007/035885, US 2006/0025806, which are incorporated by reference herein in their entirety for all purposes. Suitable commercially available vascular filters, traps or embolic protection devices are e.g. the SpiderFX™ or Fibernet® EP system. Any embolic material that by accident ends up in the delivery vessel is thus securely trapped and removed when withdrawing the combined device 200 and vascular trap.

The kit may comprise such a vascular particle trap or filter.

Figure 12A:
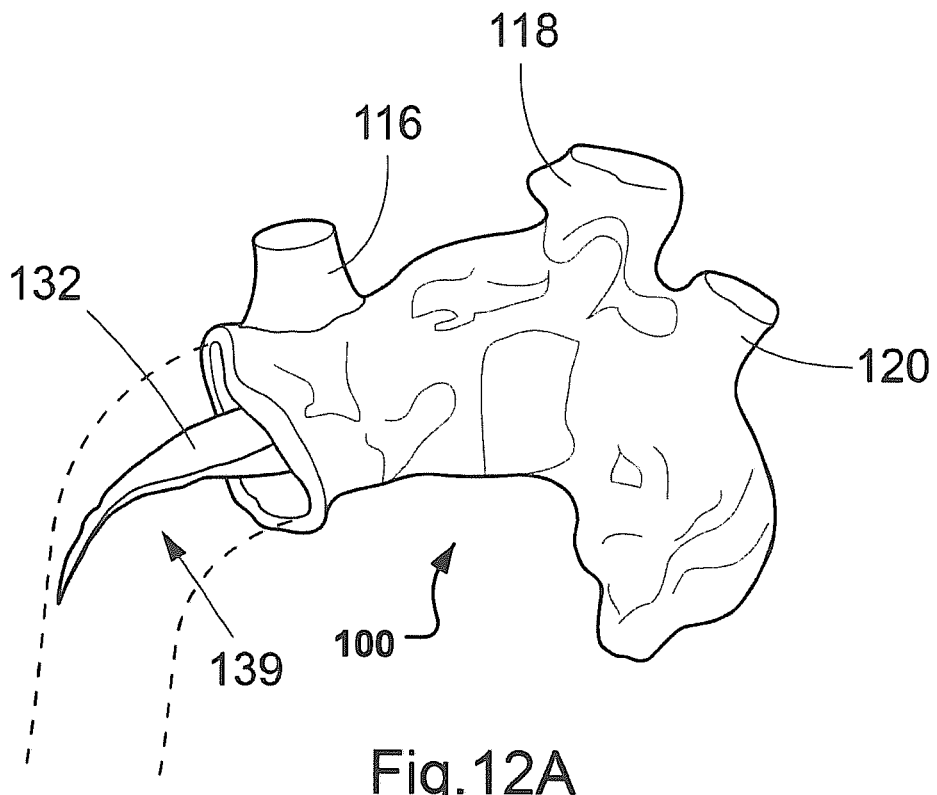
FIGS. 12A and 12B are different perspective views of schematic illustrations of a preparation of an aortic arch from animal trials performed to prove the function of the concept of embodiments of the protective device.
Figure 12B:
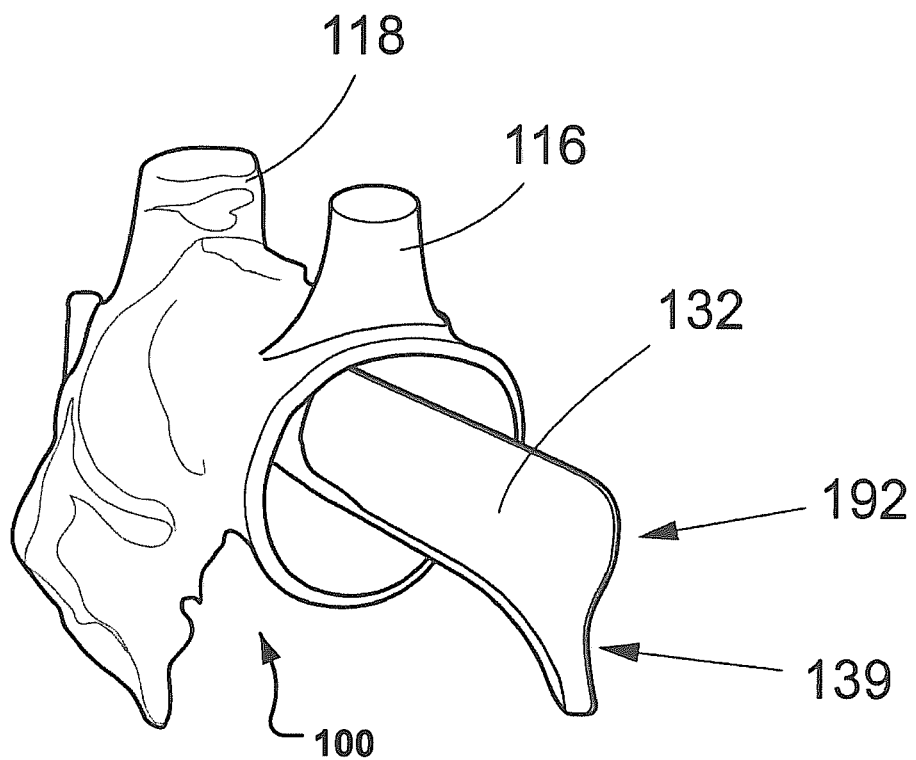

FIGS. 12A and 12B are different perspective views of schematic illustrations of a preparation of an aortic arch 100 from animal trials performed to prove the function of the concept of embodiments of the protective device. The device comprises a distal wing portion 139 at the distal end 192. Five devices were successfully positioned via the subclavian artery 120 in the aortic arch. Passage of embolic material into the carotid arteries was significantly reduced when the protection device was in place.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The present invention has been described above with reference to specific embodiments. However, other embodiments than the above described are equally possible within the scope of the invention. Different method steps than those described above may be provided within the scope of the invention. The different features and steps of the invention may be combined in other combinations than those described. The scope of the invention is only limited by the appended patent claims.

The invention claimed is:

1. An embolic protection kit for temporary protection of at least one side branch vessel of an aortic arch from embolic material, said kit comprising:
   a collapsible embolic protection device having a single connection point; and,
   a transvascular delivery unit connected to said single connection point and being adapted for delivery of said collapsible embolic protection device to a temporary placement of said collapsible embolic protection device in the aortic arch;
   wherein said embolic protection device comprises a protection unit, said protection unit comprising:
   a support member composed of a wire forming a loop and having a proximal end and a distal end, said loop expanding from a compressed shape to an expanded shape; said expanded shape having a bendable width conforming to the shape of an aortic arch; and,
   a selectively permeable unit configured for allowing passage of blood flow from said aortic arch through said selectively permeable unit into said at least one side branch vessel and preventing said embolic material from passage with said blood flow; said selectively permeable unit spanning entirely across a length and width of said loop;
   wherein said transvascular delivery unit is directly and permanently connected to said proximal end of said loop at said single connection point, wherein said single connection point is arranged directly on said loop at a periphery of said selectively permeable unit; and,
   wherein when said support member and said loop are placed across at least one side branch vessel of an aortic arch, said loop is free of contact of said aortic arch directly opposite said at least one side branch vessel.

2. The kit according to claim 1, wherein said embolic protection device is configured to extend over the ostia of a first, second and third of said side branch vessels, wherein said first side branch vessel is the left subclavian artery, the second side branch vessel is the left common carotid artery, and the third side branch vessel is the brachiocephalic artery.

3. The kit of claim 2, wherein said connection point is oriented towards said aortic side branch vessels from inside said aortic arch and at a distance from said ostia regions when said protection unit is positioned in said aortic arch.

4. The kit of claim 1, wherein said support member is shaped to be placed in apposition to tissue of a vessel wall portion of said aortic arch or releasably engage with said tissue of said vessel wall portion, and wherein said support member is formed to encircle a plurality of ostia regions of aortic side branch vessels into said aortic arch, and at a distance to said ostia regions, such that said selectively permeable unit is arranged to separate a first fluid volume of said aortic side branch vessels from a second fluid volume in said aortic arch when said protection unit is positioned in said aortic arch.

5. The kit of claim 4, wherein said support member is arranged at a perimeter of the embolic protection device, and is configured for tissue apposition in the aortic arch, wherein said support member shape is oval, elongate or patient-configured to the interior of said aortic arch.

6. The kit of claim 5, wherein said oval has an increasing width towards a distal end of the embolic protection device.

7. The kit of claim 4, wherein said selectively permeable unit is of a rigid, non-elastic material, whereby said selectively permeable unit is non-conformable to ostia regions of said side branch vessels.

8. The kit of claim 1, wherein said selectively permeable unit is devised to be arranged at a distance from ostia regions of aortic side branch vessels of said aortic arch, when said protection unit is positioned in said aortic arch, in said expanded shape.

9. The kit of claim 1, wherein the selectively permeable unit is repellant to embolic material.

10. The kit of claim 1, wherein said selectively permeable unit is stretched over the support member in a double layer configuration.

11. The kit of claim 1, wherein said protection unit is sized and shaped to extend across an apex of the aortic arch.

12. The kit of claim 1, wherein said embolic protection device has a perimeter adapted to be arranged towards tissue of the aortic arch, wherein a tissue protective unit is provided at least partly at the perimeter of the device.

13. The kit of claim 1, comprising at least one wing section shaped to extend a certain distance down into an ascendant or descendant aorta from the aortic arch, at an end portion thereof.

14. The kit of claim 1, wherein said selectively permeable unit comprises a mesh material or fabric comprising a mesh of strands.

15. The kit of claim 1, wherein said selectively permeable unit comprises a hydrophobic material and/or a hydrophobic agent.

16. The kit of claim 1, wherein said selectively permeable unit is devised to releasably trap at least a part of said embolic material from a blood flow in said aortic arch.

17. The kit of claim 1, wherein said embolic protection device comprises a safety connection for preventing loosening of the device into the descending aorta.

18. The kit of claim 1, wherein a distal portion of the embolic protection device is provided in form of an angled extension, or a nose.

19. The kit of claim 1, further comprising an introducer unit.

20. An embolic protection kit for temporary protection of at least one side branch vessel of said aortic arch from embolic material, said kit comprising:
  a collapsible embolic protection device having a single connection point; and,
  a transvascular delivery unit connected to said single connection point and being adapted for delivery of said collapsible embolic protection device to an aortic arch of a patient and temporary placement of said collapsible embolic protection device in the aortic arch;
  wherein said embolic protection device comprises a protection unit, said protection unit comprising:
  a support member forming a loop and having a proximal end and a distal end, said loop expanding from a compressed shape to an expanded shape; said expanded shape having a bendable width conforming to the shape of an aortic arch; and,
  a selectively permeable unit configured for allowing passage of blood flow from said aortic arch through said selectively permeable unit into said at least one side branch vessel and preventing said embolic material from passage with said blood flow; said selectively permeable unit spanning entirely across a length and width of said loop;
  wherein said transvascular delivery unit is directly and permanently connected to said proximal end of said loop at said single connection point, wherein said single connection point is arranged directly on said loop at a periphery of said selectively permeable unit; and,
  wherein when said support member and said loop are placed across at least one side branch vessel of an aortic arch, said loop is free of contact of said aortic arch directly opposite said at least one side branch vessel;
  wherein the delivery unit is arranged at an angle with the support member in a longitudinal direction of the embolic protection device such that a force may be applied through the delivery unit onto the embolic protection device toward a wall of the aortic arch.

21. The embolic protection kit according to claim 20, wherein said connection point is an integral of said support member.

22. A collapsible embolic protection device for temporary protection of at least one side branch vessel of an aortic arch from embolic material, said device comprising:
  a protection unit comprising:
  a support member forming a loop and having a proximal end and a distal end, said loop expanding from a compressed shape to an expanded shape; said expanded shape having a bendable width conforming to the shape of an aortic arch; and,
  a selectively permeable unit configured for allowing passage of blood flow from said aortic arch through said selectively permeable unit into said at least one side branch vessel and preventing said embolic material from passage with said blood flow; said selectively permeable unit spanning entirely across a length and width of said loop;
  wherein a transvascular delivery unit is directly and permanently connected to said proximal end of said loop at a single connection point, wherein said single connection point is arranged directly on said loop at a periphery of said selectively permeable unit; and,
  wherein when said support member and said loop are placed across at least one side branch vessel of an aortic arch, said loop is free of contact of said aortic arch directly opposite said at least one side branch vessel.

23. The device of claim 22, wherein said protection unit comprises:
  a wire;
  a cuff inflatable via an inflation lumen or self-inflatable;
  a hollow, porous, spongy, and/or resilient unit; or
  a soft and/or elastic unit in the form of a coating or surface layer arranged at least along a portion of a perimeter of said embolic protection device.

* * * * *